(12) United States Patent
Heppe

(10) Patent No.: US 9,119,916 B2
(45) Date of Patent: Sep. 1, 2015

(54) DEVICE FOR DETECTING MOISTURE FOR USE WITH A DEVICE FOR MONITORING AN ACCESS TO A PATIENT, IN PARTICULAR FOR MONITORING THE VASCULAR ACCESS IN AN EXTRACORPOREAL BLOOD TREATMENT

(75) Inventor: John Heppe, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 239 days.

(21) Appl. No.: 13/636,381

(22) PCT Filed: Mar. 23, 2011

(86) PCT No.: PCT/EP2011/001435
§ 371 (c)(1),
(2), (4) Date: Oct. 26, 2012

(87) PCT Pub. No.: WO2011/116943
PCT Pub. Date: Sep. 29, 2011

(65) Prior Publication Data
US 2013/0053754 A1 Feb. 28, 2013

(30) Foreign Application Priority Data
Mar. 23, 2010 (DE) .......................... 10 2010 012 545

(51) Int. Cl.
| | |
|---|---|
| *A61L 15/56* | (2006.01) |
| *A61M 5/168* | (2006.01) |
| *A61M 1/36* | (2006.01) |
| *A61B 5/00* | (2006.01) |

(52) U.S. Cl.
CPC ............ *A61M 5/16836* (2013.01); *A61L 15/56* (2013.01); *A61M 1/3653* (2013.01); *A61M 1/3656* (2014.02); *A61B 5/00* (2013.01)

(58) Field of Classification Search
CPC ....................................................... A61L 15/56
See application file for complete search history.

(56) References Cited

U.S. PATENT DOCUMENTS

| | | | |
|---|---|---|---|
| 3,479,565 | A | 11/1969 | Ross et al. |
| 3,631,298 | A | 12/1971 | Davis |

(Continued)

FOREIGN PATENT DOCUMENTS

| | | |
|---|---|---|
| CN | 101505812 A | 8/2009 |
| DE | 197 12 043 A1 | 10/1998 |

(Continued)

OTHER PUBLICATIONS

International Search Report from PCT/EP2011/001435 mailed on Jul. 27, 2011.

(Continued)

*Primary Examiner* — Leslie Deak
*Assistant Examiner* — Kai Weng
(74) *Attorney, Agent, or Firm* — Kenyon & Kenyon LLP

(57) ABSTRACT

A device for detecting moisture for use with a device for monitoring an access to a patient for an extracorporeal blood treatment apparatus is described. The device for detecting moisture is constituted as a two-dimensionally extending fabric to be placed on the patient's skin, having an electrically conductive structure as a moisture sensor and constituted by non-conductive and conductive warp and weft threads configured to produce in the woven fabric a defined electrically conductive structure through spatial separation of the warp and weft threads. By the use of conductive warp and weft threads, an electrically conductive structure can be constituted having sections running in different directions, thereby creating a moisture sensor exhibiting a particularly high degree of sensitivity. The electrically conductive structure is preferably terminated with a terminating resistor, preferably not a component part but rather part of a connection part of the device, so that production is simplified.

24 Claims, 21 Drawing Sheets

(56) References Cited

U.S. PATENT DOCUMENTS

| | | |
|---|---|---|
| 5,790,036 A | 8/1998 | Fisher et al. |
| 6,445,304 B1 | 9/2002 | Bandeian, Jr. et al. |
| 2002/0198483 A1 | 12/2002 | Wariar et al. |
| 2005/0038325 A1 | 2/2005 | Moll |
| 2008/0202623 A1* | 8/2008 | DeAngelis et al. ....... 139/425 R |
| 2009/0322543 A1 | 12/2009 | Crnkovich et al. |

FOREIGN PATENT DOCUMENTS

| | | |
|---|---|---|
| EP | 1 537 264 B1 | 5/2006 |
| JP | 54-133196 A | 10/1979 |
| JP | 2007-502148 A | 2/2007 |
| JP | 04-134234 B1 | 8/2008 |
| WO | 2004/004615 A1 | 1/2004 |
| WO | 2004/027132 A1 | 4/2004 |
| WO | 2005-019416 A2 | 3/2005 |
| WO | 2005/071605 A2 | 8/2005 |
| WO | 2006/008866 A1 | 1/2006 |
| WO | 2008-130149 A1 | 10/2008 |
| WO | 2009/053872 | 4/2009 |
| WO | 2009/075592 A2 | 6/2009 |

OTHER PUBLICATIONS

International Preliminary Report on Patentability from PCT/EP2011/001435 mailed on Sep. 25, 2012.

* cited by examiner

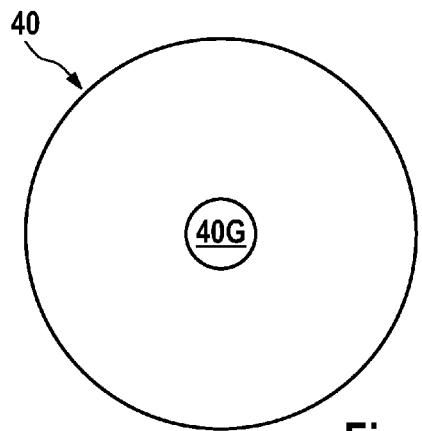
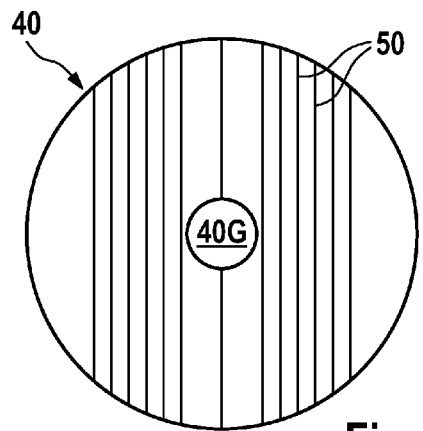
Fig. 5A
Fig. 5B
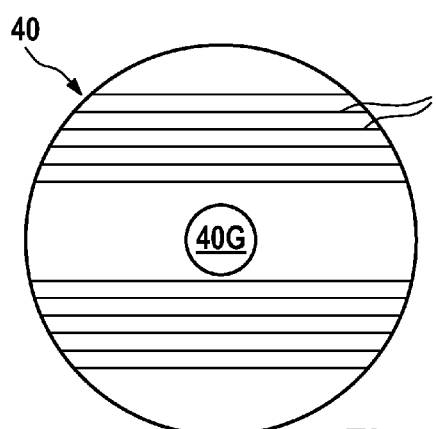
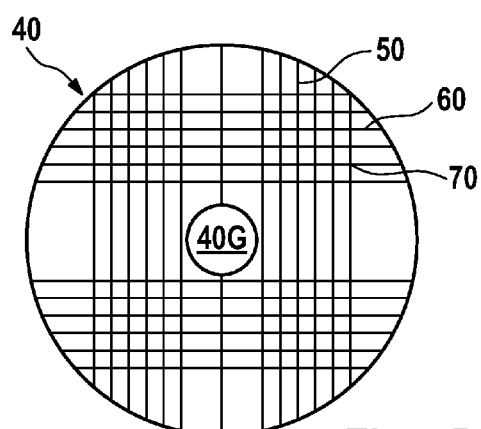
Fig. 5C
Fig. 5D
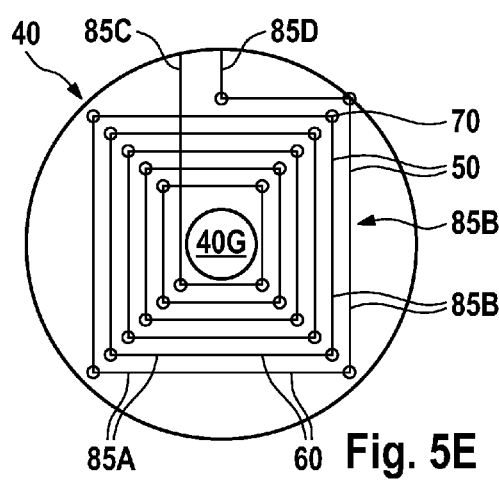
Fig. 5E

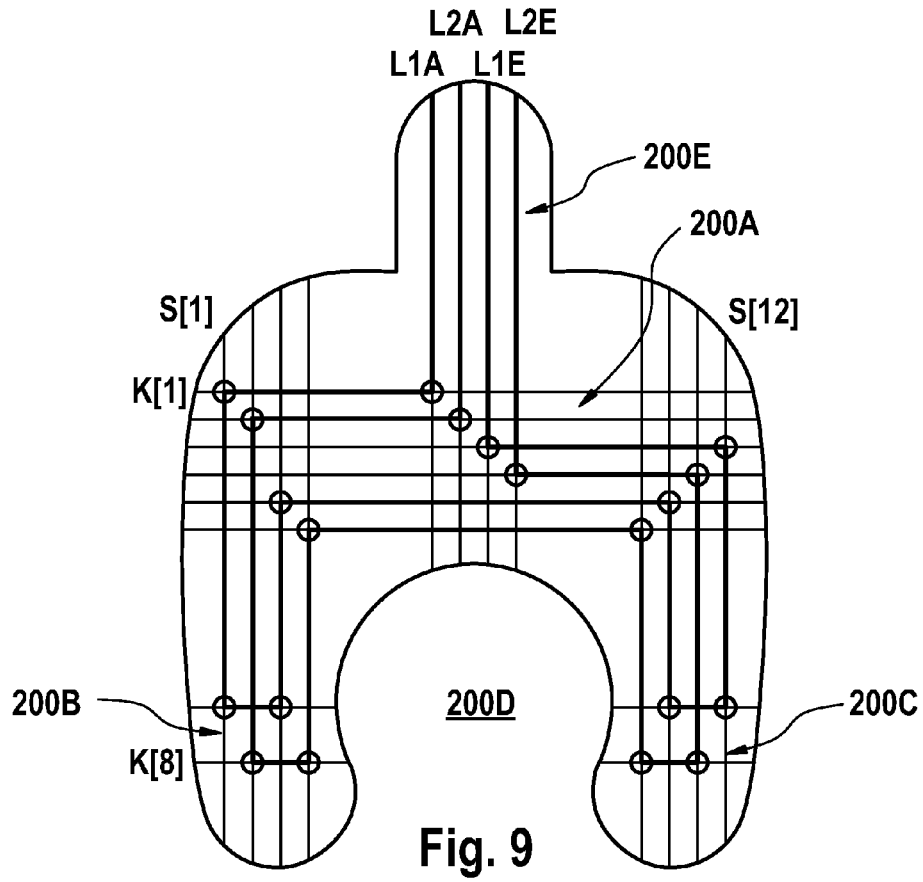

Fig. 9

| | | | | | L1A | L2A | L1E | L2E | | | | | |
|---|---|---|---|---|---|---|---|---|---|---|---|---|---|
| | S[1] | S[2] | S[3] | S[4] | S[5] | S[6] | S[7] | S[8] | S[9] | S[10] | S[11] | S[12] | |
| K[1] | Cont. | Isol. | Isol. | Isol. | Cont. | Isol. | Isol. | Isol. | Isol. | Isol. | Isol. | Isol. | |
| K[2] | Isol. | Cont. | Isol. | Isol. | Isol. | Cont. | Isol. | Isol. | Isol. | Isol. | Isol. | Isol. | |
| K[3] | Isol. | Isol. | Isol. | Isol. | Isol. | Isol. | Cont. | Isol. | Isol. | Isol. | Isol. | Cont. | |
| K[4] | Isol. | Isol. | Isol. | Isol. | Isol. | Isol. | Isol. | Cont. | Isol. | Isol. | Cont. | Isol. | |
| K[5] | Isol. | Isol. | Cont. | Isol. | Isol. | Isol. | Isol. | Isol. | Isol. | Cont. | Isol. | Isol. | |
| K[6] | Isol. | Isol. | Isol. | Cont. | Isol. | Isol. | Isol. | Isol. | Cont. | Isol. | Isol. | Isol. | |
| K[7] | Cont. | Isol. | Cont. | Isol. | | | | | Isol. | Cont. | Isol. | Cont. | |
| K[8] | Isol. | Cont. | Isol. | Cont. | | | | | Cont. | Isol. | Cont. | Isol. | Σ |
| Sum Cont. | 2 | 2 | 2 | 2 | 1 | 1 | 1 | 1 | 2 | 2 | 2 | 2 | 20 |
| Sum Isol. | 6 | 6 | 6 | 6 | 5 | 5 | 5 | 5 | 6 | 6 | 6 | 6 | 68 |

Fig. 10

DEVICE FOR DETECTING MOISTURE FOR USE WITH A DEVICE FOR MONITORING AN ACCESS TO A PATIENT, IN PARTICULAR FOR MONITORING THE VASCULAR ACCESS IN AN EXTRACORPOREAL BLOOD TREATMENT

CROSS REFERENCE TO RELATED APPLICATIONS

The present application is the national stage entry of International Patent Application No. PCT/EP2011/001435, filed on Mar. 23, 2011, and claims priority to Application No. DE 10 2010 012 545.8, filed in the Federal Republic of Germany on Mar. 23, 2010.

FIELD OF INVENTION

The present invention relates to a device for detecting moisture for use with a device for monitoring an access to a patient for an apparatus with which a fluid is fed to a patient and/or a fluid is carried away from the patient via a hose line, in particular for monitoring the vascular access in an extracorporeal blood treatment, wherein a patient's blood is carried away from the patient via an arterial hose line which has an arterial cannula and is fed to the patient via a venous hose line which has a venous puncture cannula. Moreover, the present invention relates to a device for monitoring an access to a patient, which comprises a device for detecting moisture. Furthermore, the present invention relates to a blood treatment apparatus with an extracorporeal blood circuit, which comprises an arterial hose line with an arterial cannula and a venous hose line with a venous cannula, wherein the extracorporeal blood treatment apparatus comprises a device for monitoring the arterial and/or venous vascular access. The present invention also relates to a method for the production of devices for detecting moisture for connection to a device for monitoring a patient access.

BACKGROUND INFORMATION

In the field of medical technology, various apparatuses are known with which fluids can be withdrawn from patients or fluids can be fed to patients via a hose line. The access to the patient generally takes place with a catheter for introduction into body organs or a cannula for the puncturing of vessels. During the examination or treatment, a correct access to the patient must be ensured. It is therefore necessary to monitor the patient access.

A correct access to the patient is also required particularly for extracorporeal blood treatment apparatuses which comprise an extracorporeal blood circuit. The known extracorporeal blood treatment apparatuses include for example dialysis apparatuses and cell separators, which necessitate an access to the patient's vascular system. In extracorporeal blood treatment, blood is removed from the patient with an arterial puncture cannula via an arterial hose line, the blood being fed back again to the patient with a venous puncture cannula via a venous hose line.

Despite regular monitoring of the vascular access by hospital personnel, there is in principle the risk of the puncture cannula slipping out unnoticed from the patient's blood vessel. The risk of the unnoticed slipping-out of the puncture cannula also exists in the case of home dialysis. Various devices of differing design are known for monitoring the vascular access. The known monitoring devices generally rely on the safety devices present as standard in blood treatment apparatuses, said safety devices triggering immediate interruption of the extracorporeal blood circuit in the case of an incorrect vascular access.

Devices for monitoring a vascular access are known, which comprise a device for detecting moisture in order to be able to detect the issuing of blood at the puncture point. The known devices for detecting moisture for use with the known monitoring devices for the patient access are constituted as a pad which is to be placed on the puncture point. The pad is made from an absorbent material in which a moisture sensor is embedded.

International Patent Publication No. WO 2006/008866 A1, U.S. Patent Application Publication No. 2005/0038325 A1 and U.S. Pat. No. 6,445,304 B1 describe devices for detecting moisture comprising an absorbent material which is placed on the skin. The known pads are characterised in that the moisture sensor is embedded in the absorbent material.

An electrically conductive yarn and a woven fabric comprising the electrically conductive yarn is known from European Patent No. EP 1 537 264 B1. This woven fabric is intended to be used for shielding against electromagnetic fields or for discharging static charges. The woven fabric is also intended to be used for data transmission and current supply. A further intended use of the electrically conductive yarn is to be seen in the production of strain and moisture sensors.

A non-woven fabric of synthetic fibres for shielding against electromagnetic interference sources is described in German Application No. DE 197 12 043 A1. Moreover, woven fabrics comprising a plurality of layers are known, wherein individual points of intersection of warp and weft threads form electrical contact points.

International Patent Publication No. WO 2009/075592 A2 describes a device for detecting moisture in the form of a strip of woven fabric on which or in which two parallel strip conductors are provided, between which the electrical resistance is measured. The two strip conductors are formed by conductive yarns which run only in the longitudinal direction of the strip of woven fabric. Electrical contact points between intersecting strip conductors are not provided. A drawback is that the moisture sensor has only a relatively low sensitivity on account of the form of the electrically conductive structure.

SUMMARY

An object of the present invention is to provide a device for detecting moisture with a high degree of sensitivity, which can be produced cost-effectively in large product numbers and which is easy to handle and offers a high level of wearer comfort. A further object of the present invention is to provide a device for monitoring an access to a patient with such a device for detecting moisture and an extracorporeal blood treatment apparatus with such a device for monitoring a patient access. An object of the present invention is also to provide a method for the cost-effective production of devices for detecting moisture in large product numbers.

The device according to the present invention for detecting moisture is intended for connection to a device for monitoring an access to a patient. The device according to the present invention is constituted as a two-dimensionally extending fabric to be placed on the patient's skin, said two-dimensionally extending fabric comprising an electrically conductive structure as a moisture sensor, to which the device for monitoring the patient access can be connected.

The device according to the present invention for detecting moisture is characterised in that the two-dimensionally extending fabric to be placed on the patient's skin is a textile two-dimensionally extending fabric, which is formed both by non-conductive warp and weft threads as well as conductive warp and weft threads. The conductive and non-conductive warp and weft threads are disposed in such a way that the electrically conductive structure is created. A defined electrically conductive structure is produced in the woven fabric through spatial separation of the warp and weft threads.

Decisive advantages result in practice from the use of a woven fabric for the production of the device for detecting moisture. A decisive advantage in the use of both conductive warp threads and conductive weft threads lies in the fact that an electrically conductive structure can be constituted, which comprises sections running in different directions. A moisture sensor exhibiting a particularly high degree of sensitivity can be created with such a structure.

The woven fabric has all the properties by which the device for detecting moisture to be placed on the patient's skin should be characterised. Apart from the required biocompatibility, these also include high air permeability and absorption. The device for detecting moisture constituted as a textile two-dimensionally extending fabric is soft and flexible and pleasant to wear on the skin. A high degree of biocompatibility can be achieved with a suitable selection of materials for the warp and weft threads. Since the electrically conductive structure is a component part of the woven fabric, additional materials to create an electrically conductive structure that might not have the required biocompatibility are not required. The device for detecting moisture can be produced cost-effectively in high product numbers in a conventional weaving process.

The production process of the device according to the present invention can take place with a high degree of automation. Thus, a large number of highly sensitive sensors can be produced cost-effectively with a single weaving machine on a continuous length of woven fabric, the individual sensors being able to be separated from the continuous length of woven fabric in the process or subsequently. For example, a weaving machine can produce up to 2000 sensors per second on a continuous length of woven fabric up to 3000 mm wide. Investigations have shown that the sensors produced with the method according to the present invention are largely insensitive to strip conductor breaks and exhibit high fatigue strength under reversed bending stresses The device for detecting moisture can be constituted in different forms. It can be used not only in blood treatment apparatuses which create a vascular access via a cannula or needle, but is in principle also suitable for use with catheters for the supply and removal of fluids.

In a preferred exemplary embodiment of the device for detecting moisture, the electrically conductive structure comprises a first strip conductor and a second strip conductor, the ends of the two strip conductors being constituted as terminal contacts. When the zone of the woven fabric lying between the two strip conductors comes into contact with blood, the electrical resistance measured between the two terminal contacts changes. When a terminating resistor is present, there is measured between the terminal contacts an electrical resistance which corresponds to a parallel coupling of the terminal resistance and the electrical resistance between the strip conductors. It is assumed that the blood bridges the adjacent strip conductors.

In order to increase the sensitivity of the moisture sensor, the two strip conductors are disposed lying beside one another preferably in a plurality of sections. The sensitivity is thereby increased with an increasing number of sections disposed lying beside one another. The whole of the space available on the device for detecting moisture should preferably be utilised for the moisture sensor.

An alternative exemplary embodiment provides for only one strip conductor for the electrically conductive structure, which however is constituted as a closed conductor loop and whose ends are constituted as terminal contacts.

This exemplary embodiment requires that the strip conductor has a defined resistance. The sensitivity of the moisture sensor is increased with an increasing number of sections of the closed conductor loop disposed lying beside one another. If it is not possible to set a precisely defined resistance in the production process, the resistance can also be measured initially during use of the sensor and used as a reference value. The length-specific resistance of a conductive thread may for example amount to 100 ohms per meter with a deviation of ±10%. Other values are however also possible.

It emerges from the use of a woven fabric for the production of the device for detecting moisture that the electrically conductive structure is composed of a plurality of electrically conductive sections running in a first direction and a plurality of electrically conductive sections running in a second direction, the first and second direction being at right angles to one another. One or two strip conductors running in a meandering fashion or helix-shaped can thus be produced in the woven fabric.

A particularly preferred exemplary embodiment makes provision such that the textile two-dimensionally extending fabric is constituted at least partially as a woven fabric with a plurality of layers. In the weaving process, the multi-layer woven fabric permits the electrical contacting or insulation of the electrically conductive warp and weft threads intersecting at the connection points in different planes. Particularly reliable contacting or insulation of the warp and weft threads at the points of intersection can thus be achieved.

A preferred exemplary embodiment provides a woven fabric with three layers. The three woven fabric layers can be located at all points of the sensor or only at individual points of the sensor.

The electrically conductive and electrically non-conductive warp and weft threads can be disposed in the three-layer woven fabric in such a way that a layer which is not electrically conductive to be placed on the patient's skin, a layer in which the electrically conductive sections of the strip conductor run in the first direction and a layer in which the electrically conductive sections of the strip conductor run in the second direction are formed. In order to create electrical contact points, the electrically conductive warp threads change planes in the region of the points of intersection of electrically conductive warp and weft threads, in such a way that the warp and weft threads come into contact at the points of intersection. Insulation points are created by the fact that intersecting electrically conductive warp and weft threads do not come into contact on account of a partial change of planes.

The individual sections of a strip conductor can in principle be formed by only one electrically conductive warp or weft thread. A plurality of electrically conductive warp or weft threads running beside one another can however form the strip conductor sections. A higher redundancy against tearing of the threads is thus achieved.

In the production of the woven fabric with the electrically conductive structure, zones can be structured by the fact that the textile two-dimensionally extending fabric is cut out in defined sub-zones, so that a part of electrically conductive warp and weft threads running beside one another is separated. Preferred exemplary embodiments of the present invention essentially provide for annular or cross-shaped cutouts in the textile two-dimensionally extending fabric. The cutouts can however also have any other arbitrary shape. They may lie within or at the edge of the woven fabric. The cutouts can be used not only for further structuring of the electrically conductive structure, but also for the passage of the cannula or for fixing the device for detecting moisture.

An alternative exemplary embodiment of the device for detecting moisture, in which the textile two-dimensionally extending fabric is a multi-layer woven fabric, makes provision, between the layer in which the electrically conductive sections of the strip conductor run in the first direction and the layer in which the electrically conductive sections of the strip conductor run in the second direction, for a further layer with which the warp and weft threads are electrically insulated from one another in these two planes.

The textile two-dimensionally extending fabric can have different sizes. It should on the one hand have a size which is sufficient to cover the puncture point completely, but on the other hand should not be so large that the puncture is hindered. Preferred exemplary embodiments provide a U-shaped or circular textile two-dimensionally extending woven fabric. The U-shaped woven fabric makes it possible for the device for detecting moisture to be applied even when the cannula is already in place. The circular woven fabric preferably has a central cutout for the passage of the cannula.

A further particularly preferred exemplary embodiment provides a tab on the textile two-dimensionally extending fabric, on which tab the terminal contacts are disposed.

A further particularly preferred exemplary embodiment makes provision such that the textile two-dimensionally extending fabric comprises a section with a cutout and a section with a cover for the cutout, wherein the electrically conductive structure is constituted such that the textile two-dimensionally extending fabric is sensitive to moisture at the upper side. An advantage of this exemplary embodiment lies in the fact that the cutout of the textile two-dimensionally extending fabric, in which the cannula lies, can be covered by the cover. For this purpose, the section with the cover is simply folded onto the section with the cutout. The moisture sensor is then sensitive on both sides.

The device according to the present invention for monitoring an access to a patient, in particular for monitoring the vascular access in an extracorporeal blood treatment, comprises the device according to the present invention for detecting moisture. The monitoring device preferably comprises an evaluation unit which can be connected to the device for detecting moisture and which, in the event of detecting moisture, emits an acoustic, optical and/or tactile alarm. A control signal can also be generated for an intervention into the control of the apparatus with which a fluid is fed to the patient and/or a fluid is carried away from the patient via the hose line.

The monitoring device preferably comprises a connection part, at which the device for detecting moisture is connected in order to produce an electrical connection between the evaluation unit of the monitoring device and the moisture sensor of the device for detecting moisture. The connection part of the monitoring device is preferably connected electrically to the evaluation unit via a connection cable of sufficient length. Alternatively, however, a wireless connection can also be established.

A terminating resistor is not provided in the exemplary embodiment of the device for detecting moisture which comprises one strip conductor with two terminal contacts, said strip conductor being constituted as a closed conductor loop. In the exemplary embodiment with two strip conductors, two ends of the strip conductors are connected to one another via a terminating resistor and the other ends of the strip conductors are connected electrically to the evaluation unit of the monitoring device. In the exemplary embodiment with the two strip conductors, the terminating resistor makes it possible to check the device for detecting moisture for its operability by means of a resistance measurement between the terminal contacts. In the case of an operable moisture sensor, a resistance is measured between the terminal contacts that corresponds to the sum of the terminal resistance and the strip conductor resistance.

In the exemplary embodiment with the two strip conductors connected via a terminating resistor, it is particularly advantageous if the terminating resistor is not a component part of the device for detecting moisture, but rather a component part of the monitoring device. This has an advantage that a terminating resistor does not have to be provided on the woven fabric or in the woven fabric. Furthermore, it is advantageous for the terminating resistor not to be discarded after the replacement of the device for detecting moisture, which is intended for one-off use. It is also advantageous that a separate terminating resistor can be reproduced more easily than a resistor on or in the woven fabric. A printed terminating resistor, for example, is subject to much larger manufacturing tolerances. The manufacturing tolerance of, for example, miniature resistors (SMD resistors), on the other hand, can be less than 1% of the nominal resistance value. It is also advantageous that the resistance value of a separate terminating resistor, in contrast with a printed resistor, cannot change due to reversed bending stresses during the dialysis treatment.

Since the terminating resistor is not a component part of the device for detecting moisture, conventional resistors can be used, in particular miniature resistors (SMD resistors), which are cost-effective and have small component tolerances. In addition, the terminal resistance cannot change if the device for detecting moisture is exposed to liquid. Furthermore, a further production step is dispensed with in the production of the device for detecting liquid. In addition, no solvents, pastes or the like are required in the production of the woven moisture sensor, as a result of which the biocompatibility is increased.

In a particularly preferred exemplary embodiment, the terminating resistor is located in the connection part of the monitoring device. In a particularly preferred exemplary embodiment, the connection part comprises four terminal contacts, the connection cable for producing an electrical connection between the evaluation unit of the monitoring device and the device for detecting moisture being connected to the first and second terminal contact, and the third and fourth terminal contact being connected electrically to one another via the terminating resistor. The sequence in which the terminal contacts are disposed is arbitrary. An important point is that a current source can be connected to two terminal contacts and a terminating resistor can be connected to two terminal contacts.

The connection part is preferably constituted as a clamping device for clamping the textile two-dimensionally extending fabric of the device for detecting moisture. The clamping device preferably comprises elements with which the device for detecting moisture is orientated and/or fixed in such a way that the terminal contacts of the device for detecting moisture lie opposite the corresponding terminal contacts of the connection part of the monitoring device. These elements can be constituted as cutouts corresponding to the shape of the device for detecting moisture or as protrusions corresponding to the shape of the cutouts of the device for detecting moisture. The fixing can take place by keyed connection, force-locked connection or friction-locked connection. The terminal contacts of the connection part of the monitoring device themselves can also be constituted as elements for the fixing. The terminal contacts can for example be spikes penetrating into the woven fabric.

The device according to the present invention for monitoring a patient access can form a separate unit or be a component part of the apparatus with which a fluid is fed to the patient and/or carried away from the patient, in particular a component part of the extracorporeal blood treatment apparatus. If the monitoring device according to the present invention is a component part of the blood treatment apparatus, the monitoring device can make use of specific subassemblies or components which are in any case present in the blood treatment apparatus.

The side of the device for detecting moisture which is to be placed on the patient's skin is preferably covered with a preferably moisture-impermeable adhesive layer for fixing the device for detecting moisture on the skin. A covering material covering the layer, which can easily be pulled off from the carrier material, is preferably applied on the adhesive layer.

In the production of the device for detecting moisture, it may be advantageous that, on the continuous lengths of woven fabric, the adhesive layer can easily be deposited continuously together with the covering layer onto the textile two-dimensional extending fabric in the weaving process. The devices for detecting moisture are then available as a rolled product and merely need to be separated from one another. The individual devices for detecting moisture are preferably cut out or stamped out in the desired shape directly after the application of the adhesive layer and the covering material.

Instead of the adhesive layer, a preferably moisture-impermeable adhesive film, for example a PET film, can be applied onto the woven fabric. The adhesive film on the one hand has an advantage that a barrier can be created against saturation of the woven fabric with the patient's perspiration, and on the other hand a different adhesive force can be provided at the upper and lower side.

At the side facing the patient's skin, the film preferably has a lower adhesive force than at the side facing away from the skin and facing the woven fabric.

Various exemplary embodiments of the present invention will be explained below in greater detail with reference to the accompanying drawings.

BRIEF DESCRIPTION OF THE DRAWINGS

FIG. 5A shows the first woven fabric layer of a further exemplary embodiment of the device for detecting moisture.

FIG. 5B shows the second woven fabric layer.

FIG. 5C shows the third woven fabric layer.

FIG. 5D shows a representation of the conductive warp and weft threads of the second and third woven fabric layers.

FIG. 5E shows a representation of the strip conductor of the device for detecting moisture.

FIG. 9 shows a further exemplary embodiment of the device for detecting moisture in a schematic representation.

FIG. 10 shows a matrix to illustrate the points of intersection of the warp and weft threads of the device for detecting moisture of FIG. 9.

DETAILED DESCRIPTION

Figure 1:
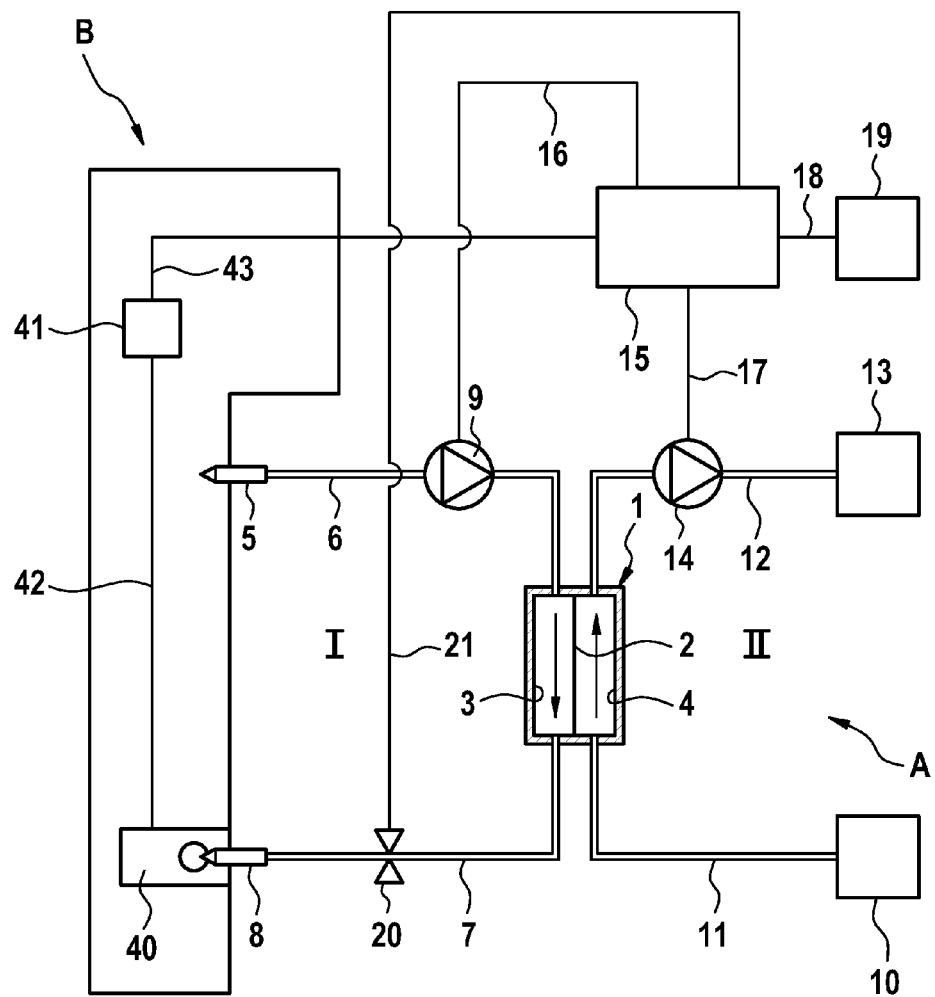
FIG. 1 shows the main components of a blood treatment apparatus, which comprises an exemplary device for monitoring the arterial and venous vascular access.

FIG. 1 shows the main components of a blood treatment apparatus, in particular haemodialysis apparatus A, which comprises a device B for monitoring the venous and arterial vascular access. In the present exemplary embodiment, monitoring device B is a component part of haemodialysis apparatus A. The dialysis apparatus will first be described by reference to FIG. 1.

Haemodialysis apparatus A comprises a dialyser 1, which is divided by a semipermeable membrane 2 into a blood chamber 3 and a dialysing fluid chamber 4. An arterial hose line 6 is connected by means of an arterial puncture cannula 5 to the fistula or the shunt of the patient, said arterial hose line leading to the inlet of blood chamber 3 of the dialyser. Leading away from the outlet of blood chamber 3 of dialyser 1 is a venous hose line 7, which is connected by means of a venous puncture cannula 8 to the fistula or the shunt of the patient. A blood pump 9, which conveys the blood in extracorporeal blood circuit I, is incorporated into arterial hose line 6

Dialysing fluid circuit II of dialysis apparatus A comprises a dialysing fluid source 10, to which a dialysing fluid supply line 11 is connected, which leads to the inlet of dialysing fluid chamber 4 of the dialyser. Departing from the outlet of dialysing fluid chamber 4 of dialyser 1 is a dialysing fluid discharge line 12, which leads to a drain 13. A dialysing fluid pump 14 is incorporated into dialysing fluid discharge line 12.

The control of the dialysis apparatus is assumed by a central control unit 15, which controls blood pump and dialysing fluid pump 9, 14 via control lines 16, 17. Central control unit 15 is connected via a data line 18 to an alarm unit 19, which emits an optical, acoustic and/or tactile alarm in the event of a malfunction.

Located downstream of blood chamber 3 of dialyser 1 on venous hose line 7 is an electro-magnetically actuated hose clamp 20, which is closed via a further control line 21 by central control unit 15 if the venous puncture cannula (needle) slips out of the vascular access and the moisture sensor becomes moistened with blood. Moreover, control unit 15 stops blood pump 9 after the slipping-out of the cannula when the sensor becomes moistened.

In the present exemplary embodiment, monitoring device B is used to monitor the venous vascular access. Monitoring device B comprises a device 40 for detecting moisture, which is disposed at the puncture point. This detection device 40 is represented only schematically in FIG. 1. The monitoring device also comprises an evaluation unit 41 which is connected electrically via a connection line 42 to detection device 40.

Evaluation unit 41 is connected via a data line 43 to central control unit 15 of dialysis apparatus A. In the event of blood issuing from the venous cannula and/or the puncture point and moistening the moisture sensor, evaluation unit 41 of monitoring device B generates a control signal, which is received via data line 43 by central control unit 15, which undertakes an intervention into the blood treatment. Control unit 15 stops blood pump 9 and closes hose clamp 20. Moreover, the control unit generates an alarm signal, so that alarm unit 19 emits an acoustic, optical and/or tactile alarm. The data can also be transmitted wirelessly between monitoring device B and dialysis apparatus A.

A first exemplary embodiment of device 40 for detecting moisture to be placed on the patient's skin at the puncture point is described below. Detection device 40 is constituted as a pad of a textile two-dimensionally extending fabric (woven fabric) to be placed on the patient's skin. In the first example of embodiment, textile two-dimensionally extending fabric 100 is a multi-layer woven fabric, which comprises three layers (planes).

Figure 2:
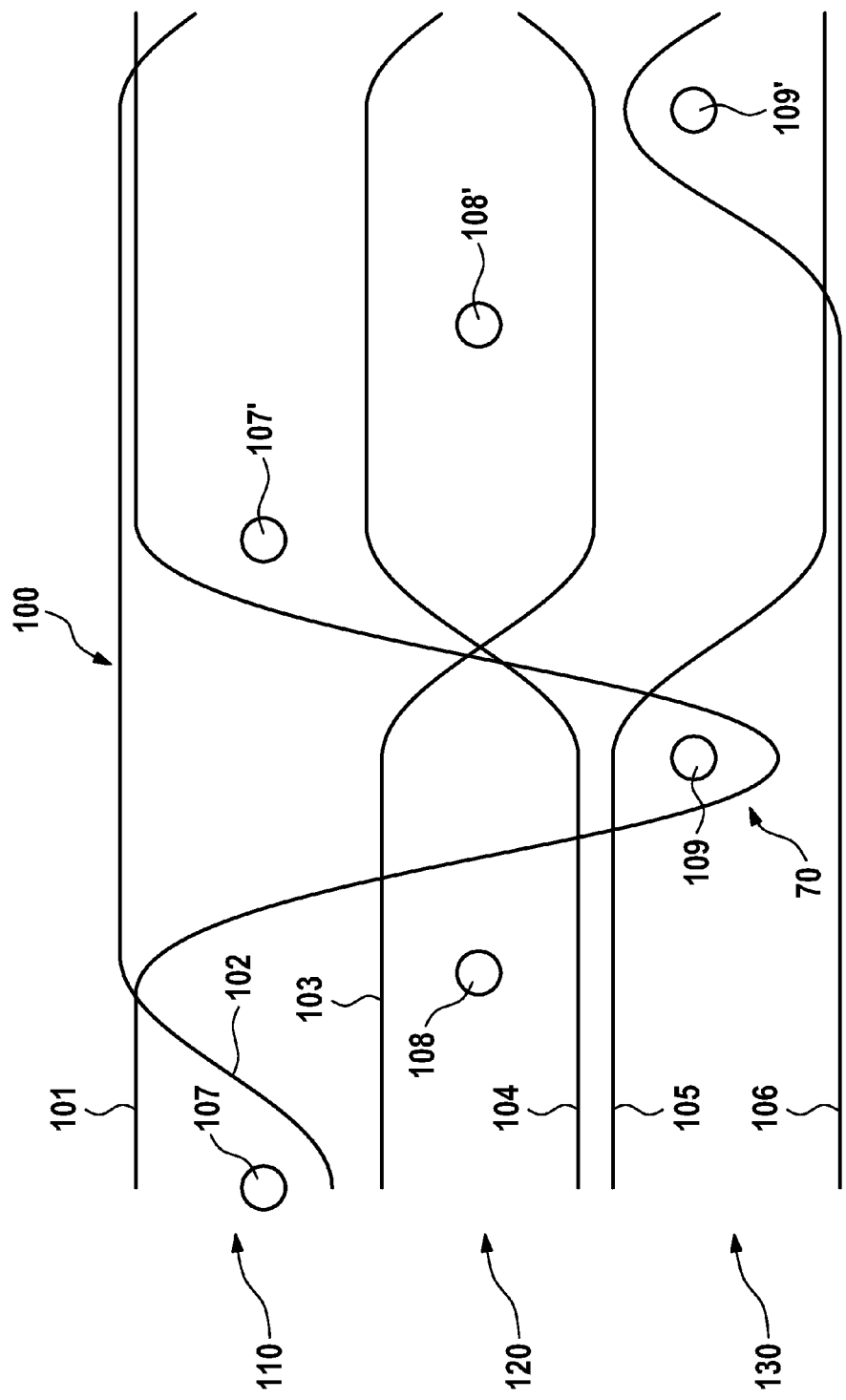
FIG. 2 shows a cross-section through the woven fabric.

FIG. 2 shows a warp section through 3-layer woven fabric 100. The warp threads running from left to right are represented in FIG. 2. The warp section shows a total of 6 warp threads 101-106. The number of layers of the woven fabric is defined according to the number of planes 110, 120, 130 in which weft threads 107, 108, 109; 107', 108', 109' lie. Weft threads 107, 108, 109; 107', 108', 109' lying essentially at right angles to the warp threads in the three planes 110, 120, 130 are marked by circles. The production of a three-layer woven fabric is known to the person skilled in the art. During weaving, weft threads 107, 108, 109; 107', 108', 109' lie on three planes 100, 110, 120. Warp threads 101-106 are fed on three planes. Each individual warp thread can be respectively raised or lowered out of the three warp thread planes in order to enable the interweaving of a weft thread. Out of originally 60 threads/cm, on one plane, 20 threads are fed in an upper plane, 20 threads are fed in a middle plane and 20 threads are fed in a lower plane in production in the case of the three-layer woven fabric. The number of 60 threads/cm represents a common example, but can also diverge from this.

In the weaving process, weft threads 107, 108, 109; 107', 108', 109' do not necessarily have to be fed in planes lying above one another, but rather the position of a weft thread in a plane can also arise in the weaving process through "jumping back" of the raised or lowered warp threads, which automatically pull the weft thread into a defined plane. The planes are always to be understood as "imaginary" layers which do not have to be "flat".

In the present exemplary embodiment, detection device 40, which will also be referred to below as a pad, has the shape of a U. U-shaped pad 40 comprises a central zone 40A with two legs 40B, 40C, which laterally enclose a semicircular cutout 40D. A tab 40E lying opposite the two legs 40B, 40C is formed on central section 40A.

The multi-layer woven fabric is made from electrically conductive and electrically non-conductive warp and weft threads (monofilaments, carbon fibres, silvered polyamide yarn). The electrically conductive and electrically non-conductive warp and weft threads are disposed in such a way that the woven fabric comprises a lower layer to be placed on the patient's skin, a middle layer and an upper layer facing away from the patient's skin.

Figure 3A:
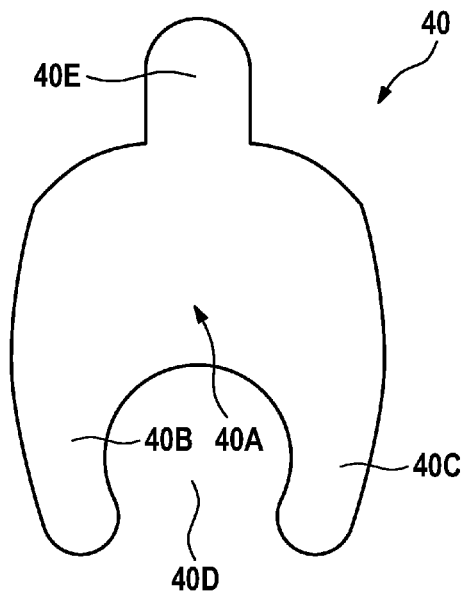
FIG. 3A shows a schematic representation of the first woven fabric layer of a first exemplary embodiment of the device for detecting moisture.

FIG. 3A shows the lower layer of the woven fabric. The lower woven fabric layer is electrically non-conductive. No electrically conductive warp and weft threads are present in this plane. The lower layer can however also be dispensed with. The electrically conductive warp and weft threads are located in the middle and upper plane. The conductive and non-conductive warp and weft threads form an electrically conductive structure in these two planes. The electrically conductive structure involves two strip conductors, which each extend over the whole pad. Both strip conductors consist of sections running respectively at right angles to one another, as is explained below.

Figure 3B:
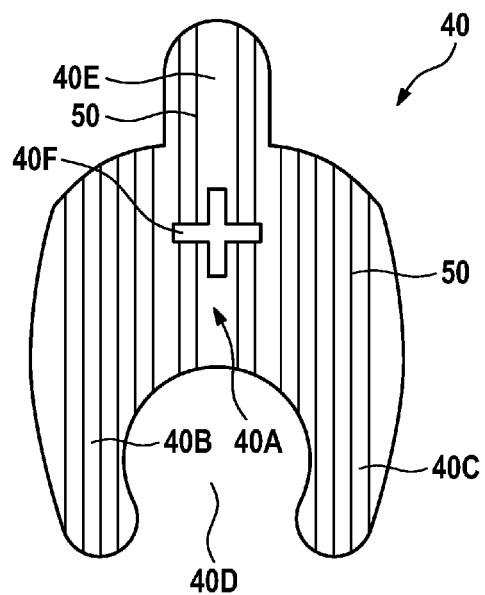
FIG. 3B shows a schematic representation of the second woven fabric layer of the device for detecting moisture.

FIG. 3B shows the middle layer of the woven fabric. Electrically conductive warp threads 50, which lie in the middle plane, are marked by vertical lines. These warp threads form the sections of the two strip conductors running in a first direction, when they are "assigned" to a strip conductor by the creation of suitable contact and insulation points.

Figure 3C:
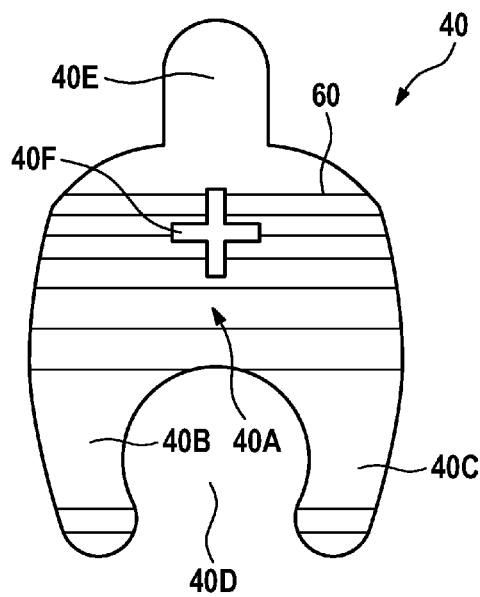
FIG. 3C shows a schematic representation of the third woven fabric layer of the device for detecting moisture.

FIG. 3C shows the upper layer of the woven fabric. Electrically conductive weft threads 60 are marked by horizontal lines. These weft threads form the sections of the two strip conductors which extend in the second direction running at right angles to the first direction, when they are "assigned" to a strip conductor by the creation of suitable contact and insulation points.

Figure 3D:
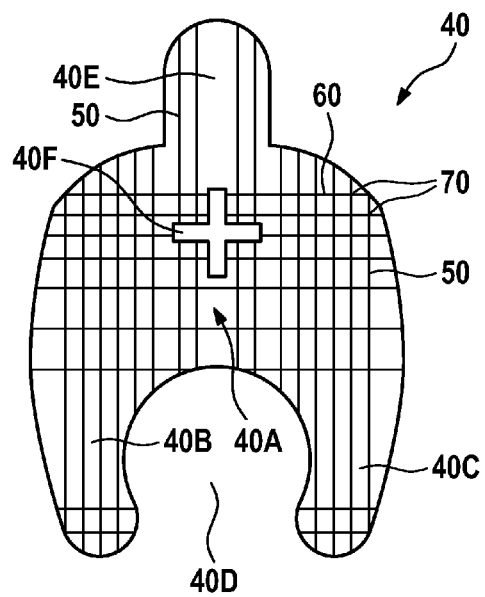
FIG. 3D shows a schematic representation of the second and third woven fabric layers of the device of FIG. 3B and FIG. 3C.

In FIG. 3D, electrically conductive warp and weft threads 50, 60 of the woven fabric are marked by vertical and horizontal lines. A grid-shaped structure of electrically conductive threads arises.

The two strip conductors 80, 90 are formed in the middle and upper plane of the woven fabric by the fact that electrically conductive warp and weft threads 50, 60 are disposed at points of intersection 70 in such a way that they are either connected to one another in an electrically conductive manner or are insulated electrically from one another. A contact point between electrically conductive warp and weft threads is achieved by means of a partial change of plane of the warp thread during the weaving process, as can be seen from FIG. 2.

FIG. 2 shows weft threads 107, 108, 109; 107', 108', 109' lying in three planes 110, 120, 130. As a result of the partial change of electrically conductive warp thread 101, for example from upper plane 110 into lower plane 130, an electrical connection is produced between this warp thread 101 and electrically conductive weft thread 109 in the lower plane which crosses warp thread 101. Without the partial change of planes, electrically conductive warp and weft threads are insulated from one another. For example, electrically conductive warp thread 102 is not electrically connected to electrically conductive weft thread 109, since warp thread 102 does not partially change plane in the region of weft thread 109.

Figure 3E:
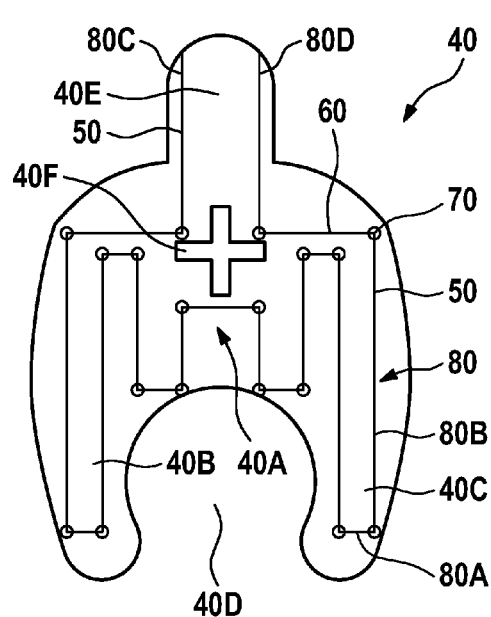
FIG. 3E shows a schematic representation of the first strip conductor.

In FIG. 3E, the electrical contact points at points of intersection 70 between electrically conductive warp threads 50 of FIG. 3B and electrically conductive weft threads 60 of FIG. 3C are represented as circles. There emerges as strip conductor 80 a closed conductor loop, which runs from tab 40E via central zone 40A to left-hand leg 40B and from left-hand leg 40B via central zone 40A to right-hand leg 40C and from right-hand leg 40C via central zone 40A back to tab 40E of pad 40. Straight sections 80A, 80B of first strip conductor 80 at right angles to one another can clearly be seen. The two ends of strip conductor 80 form the two terminal contacts 80C, 80D of first strip conductor 80. Both terminal contacts 80C, 80D lie at the outer side of tab 40E.

Figure 3F:
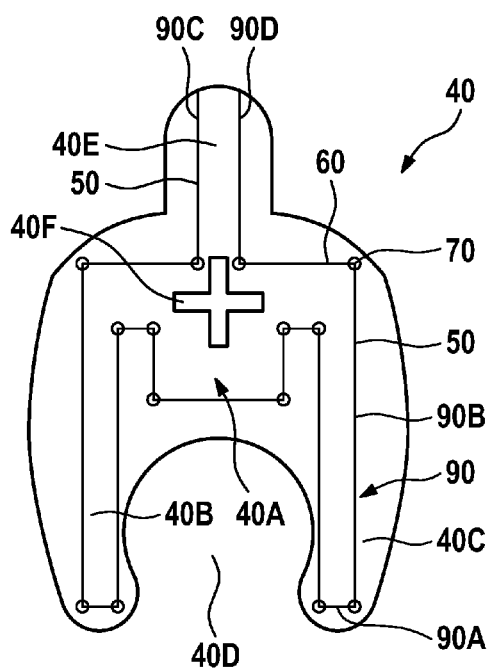
FIG. 3F shows a schematic representation of the second strip conductor.

Second strip conductor 90 with sections 90A, 90B running normal to one another is represented in FIG. 3F. It again runs from tab 40E via central zone 40A to left-hand leg 40B and from left-hand leg 40B via central zone 40A to right-hand leg 40C and from right-hand leg 40C via central zone 40A to tab 40E of pad 40. The two ends of the second strip conductor 90 form a second pair of terminal contacts 90C, 90D, which are disposed on tab 40E between terminal contacts 80C, 80D of first strip conductor 80.

Figure 3G:
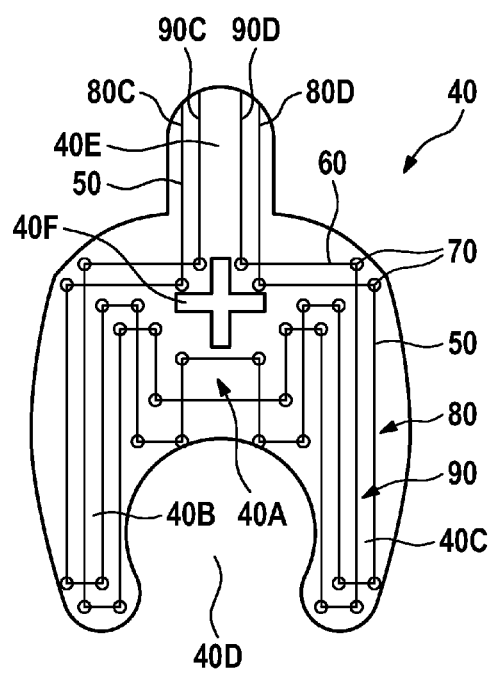
FIG. 3G shows a representation of the strip conductors of the second and third woven fabric layers.

FIG. 3G shows the two strip conductors 80, 90 together with the contact points. Individual sections 80A, 80B, 90A, 90B of the two strip conductors 80, 90 are disposed in such a way that they run essentially parallel to one another.

For the sake of better clarity, FIGS. 3E to 3G show only the sections of the conductive warp and weft threads that form the strip conductors. The warp and weft threads, however, run through the woven fabric over the whole width and length.

Figure 3H:
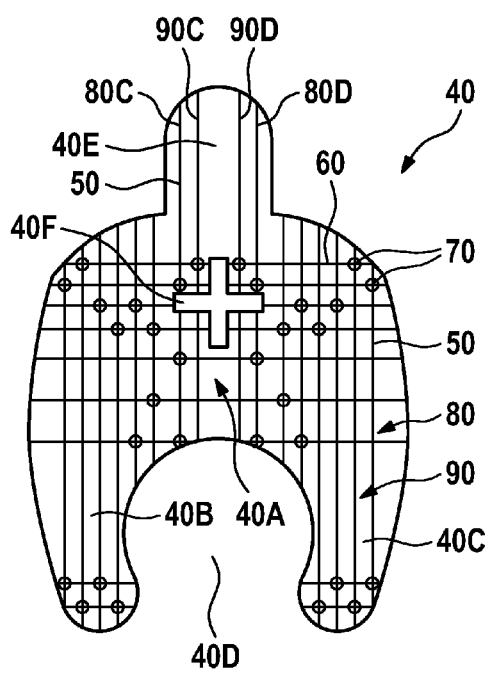
FIG. 3H shows a representation of the continuous electrically conductive warp and weft threads with the strip conductors of the second and third woven fabric layers.

FIG. 3H shows, for the purpose of illustration, electrically conductive warp and weft threads 50, 60 of the two strip conductors 80, 90 over their whole length. The intersecting warp and weft threads come into contact, but only at the contact points represented by circles.

In the present exemplary embodiment, the electrically conductive warp and weft threads are severed on the one hand by semi-circular cutout 40D. On the other hand, the conductive warp and weft threads are severed by a further cutout 40F, which is located in central section 40A of pad 40. In the present exemplary embodiment, this cutout is a cross-shaped cutout 40F. This cutout can however also have any other arbitrary shape. The crucial factor is that, with one or more additional cutouts, an electrical structure of a specific configuration, in which individual conductive threads are severed, can be created in a targeted manner.

The in particular cross-shaped cutout 40F serves on the one hand for the targeted, subsequent and permanent interruption of the conductive threads in the finished woven fabric, so that only a single strip conductor path remains in the finished product. It is intended with cutout 40F to avoid redundant strip conductor paths remaining. On the other hand, cutout 40F, in combination with a suitably formed protrusion, can be used for the fixing of the terminal contacts by a keyed connection.

Semicircular cutout 40D is used for the passage of the puncture cannula, pad 40 also being able to be placed on the patient's skin when the puncture cannula is already in place. Central cutout 40F can be used for the orientation and/or fixing of the pad in a suitable holding or clamping part, which however is not represented in the figures.

Further exemplary embodiments of the pad are described below, which however differ from the exemplary embodiment described by reference to FIGS. 3A-3H solely by the shape of the pad and the electrical structuring. All the exemplary embodiments are based on the same basic principle of connecting electrically to one another or insulating electrically from one another at the points of intersection electrically conductive warp and weft threads in a woven fabric of electrically conductive and electrically non-conductive warp and weft threads by means of the targeted creation of contact points or insulation points.

FIGS. 4A-4I show a second exemplary embodiment of U-shaped pad 40, which however does not comprise a central cutout. The course of the two strip conductors differs from the strip conductor course of the first exemplary embodiment. The elements corresponding to one another are provided with the same reference numbers. In the second exemplary embodiment, a further insulation plane is provided, which separates from one another the electrically conductive warp and weft threads of the planes lying above or below the latter. This can be seen with the aid of FIGS. 4A-4I.

Figures 4A, 4B:
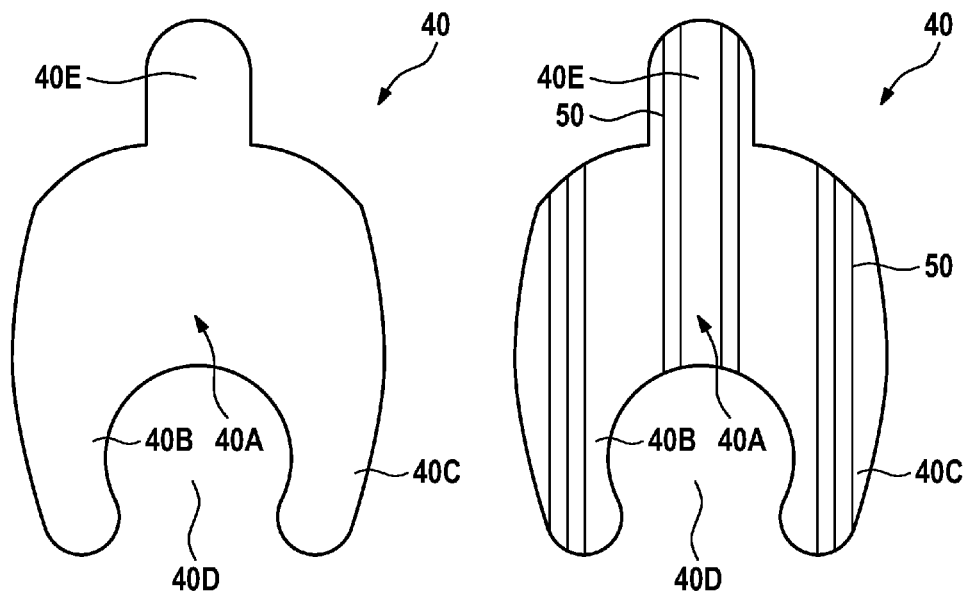
FIG. 4A shows the first woven fabric layer of a second exemplary embodiment of the device for detecting moisture with a further insulating woven fabric layer.
FIG. 4B shows the second woven fabric layer of the device the detecting moisture.
Figures 4C, 4D:
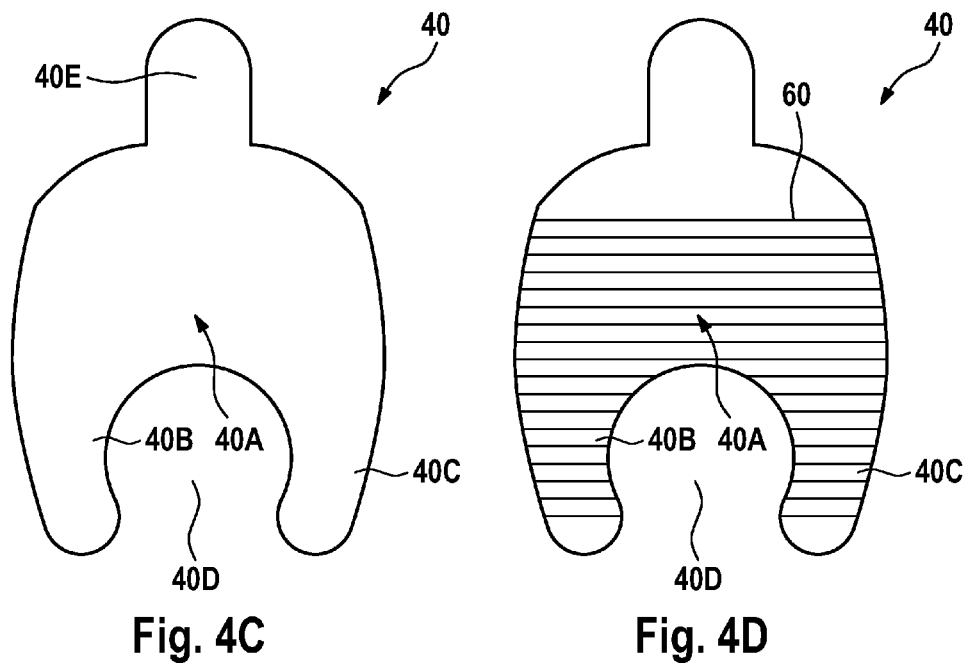
FIG. 4C shows the insulating third woven fabric layer.
FIG. 4D shows the fourth woven fabric layer.
Figure 4E:
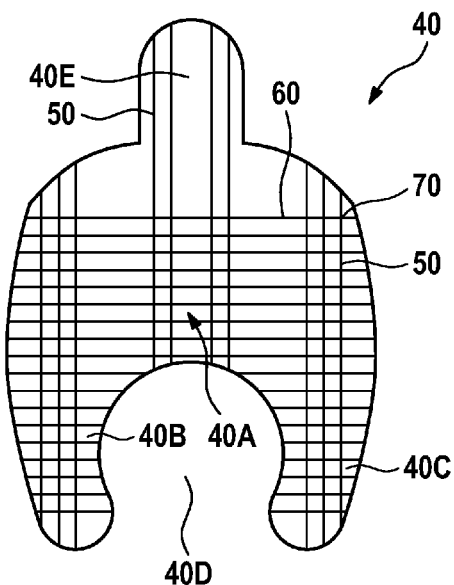
FIG. 4E shows a representation of the electrically conductive warp and weft threads of the second and fourth woven fabric layers.

FIG. 4A shows the first layer of the pad to be placed on the patient's skin, said layer not being electrically conductive. Lying on the first plane is a second plane with electrically conductive warp threads 50 (FIG. 4B). Lying on the plane with the electrically conductive warp threads is a third plane which is not electrically conductive, since electrically conductive warp and weft threads do not come into contact (FIG. 4C). Lying on the third plane is a fourth plane with electrically conductive weft threads 60. Electrically conductive warp and weft threads 50, 60 are disposed at a differing distance from one another in the second and fourth plane, so that the structure represented in FIG. 4E results.

Figure 4F:
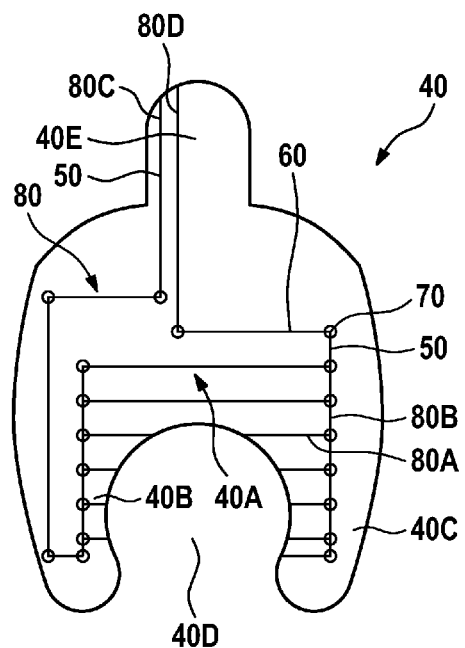
FIG. 4F shows a schematic representation of the first strip conductor.
Figure 4G:
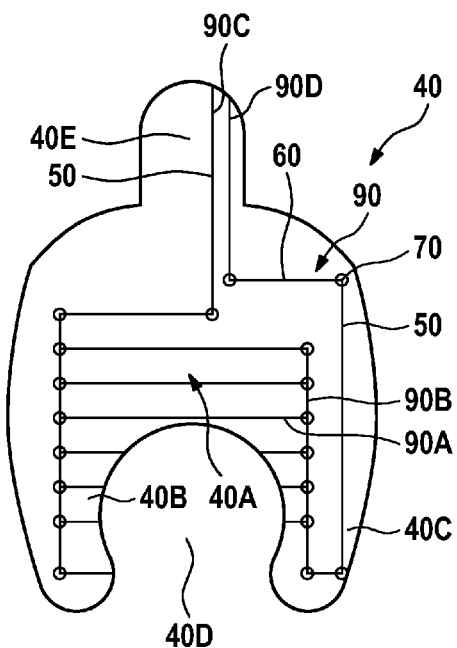
FIG. 4G shows a schematic representation of the second strip conductor.

FIG. 4F shows electrically conductive warp and weft threads 50, 60 which form first strip conductor 80, whilst FIG. 4G shows electrically conductive warp and weft threads 50, 60 which form second strip conductor 90. FIGS. 4F and 4G show that semicircular cutout 40D interrupts a part of sections 80A, 90A of first and second strip conductors 80, 90, said sections running parallel to one another between two electrical connection points and forming a parallel circuit of electrically conductive threads. In this exemplary embodiment, both first and second strip conductors 80, 90 each comprise a strip conductor section which is formed by more than two threads. Consequently, the first and second strip conductor cannot be interrupted even when one of the at least two threads of this strip conductor section tears. The figures are intended to illustrate that the redundancy can be increased or reduced by the number and configuration of the cutouts in the pad. In order to increase the redundancy, the number of electrically conductive warp on weft threads, which form a parallel circuit, can be increased in individual or all strip conductor sections of the strip conductor, whilst the number of warp and weft threads of individual or all strip conductor sections can be reduced in order to reduce the redundancy.

A high redundancy of the strip conductors, i.e., a plurality of conductive threads, leads to a high degree of sensitivity of the moisture sensor, because even small quantities of blood between the strip conductors lying close beside one another can be detected at every point of the sensor. A low or no redundancy conversely gives rise to a low sensitivity. A drawback of a high redundancy, however, is that, in the event of a break in the strip conductor, the malfunction of an unchecked sensor is not detected until it is used, unless each individual strip conductor has been previously checked for its integrity. In the case of sensors with redundancy, therefore, an in-process control (IPC) takes place, in which each individual strip conductor is examined in the production process for its operability.

In the case of sensors which have no redundancy, an in-process control (IPC) can also be carried out, in which each individual strip conductor is examined in the production process for its operability.

If threads with high tear strength are used in the woven fabric, an electrical structure with a lower redundancy may be sufficient, whereas an electrical structure with a high redundancy is advantageous when use is made of threads with lower tear strength.

Moreover, the operability of the moisture sensor can be checked by measuring the resistance between the terminal contacts. If a strip conductor section comprising only one conductive thread is interrupted, an infinitely high resistance is measured. In the case of an interruption of a thread in a strip conductor section comprising a plurality of threads forming a parallel circuit, the defect of an individual thread cannot however be detected by measuring an infinitely high resistance.

Figure 4H:
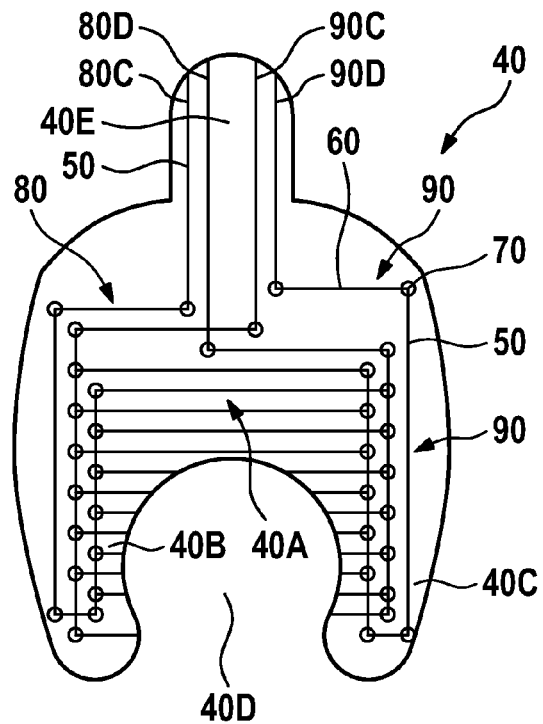
FIG. 4H shows a representation of the strip conductors of the second and fourth woven fabric layers.
Figure 4I:
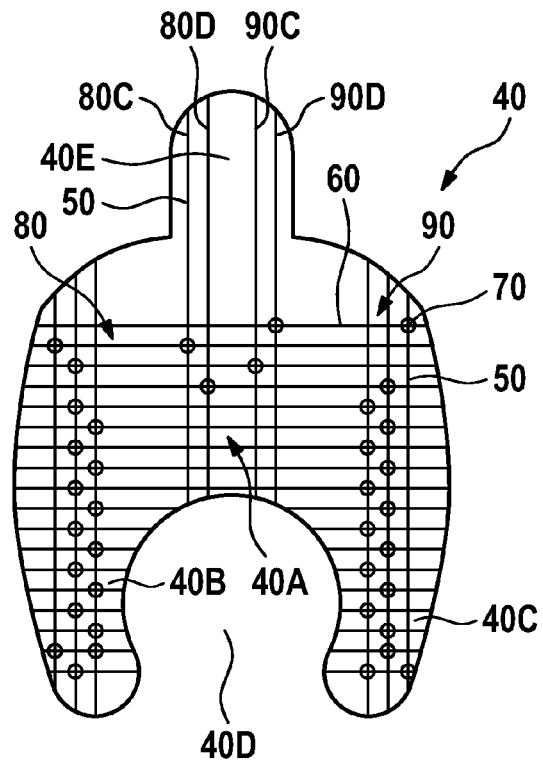
FIG. 4I shows a representation of the strip conductors of the second and fourth woven fabric layers together with the continuous electrically conductive warp and weft threads.

FIG. 4H shows, for the purpose of further illustration, two strip conductors 80, 90 with respective terminal contacts 80C, 80D, 90C, 90D on tab 40E of pad 40. FIG. 4I shows warp and weft threads 50, 60 forming the two strip conductors 80, 90 over the whole length.

For the sake of better clarity, FIGS. 4F to 4H again show only the sections of the conductive warp and weft threads that form the strip conductors. The warp and weft threads, however, run through the woven fabric over the whole width and length.

Figure 5F:
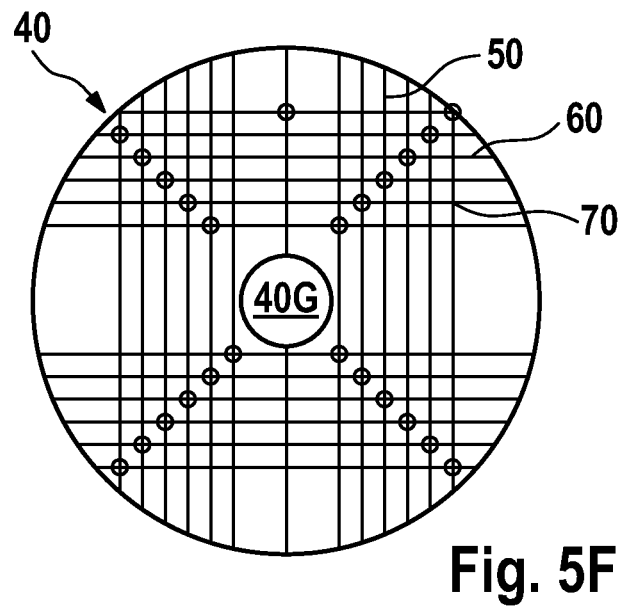
FIG. 5F shows a representation of the strip conductor together with the continuous warp and weft threads.

FIGS. 5A-5F show a further exemplary embodiment of pad 40, wherein the same reference numbers are used for elements corresponding to one another. In this exemplary embodiment, pad 40 is circular and comprises a central circular cutout 40G for the passage of the cannula. Moreover, this exemplary embodiment differs from the exemplary embodiments described by reference to FIGS. 3 and 4 by the fact that only one strip conductor 85 in the form of a meandering closed conductor loop is provided (FIG. 5E).

Pad 40 comprises a three-layer woven fabric with a lower layer (FIG. 5A), which is not electrically conductive, a middle layer (FIG. 5B) with electrically conductive warp threads 50 and an upper layer (FIG. 5C) with electrically conductive weft threads 60. Intersecting warp and weft threads 50, 60 of the middle and upper plane are represented in FIG. 5D. FIG. 5E shows the contact points, represented as circles, between electrically conductive warp and weft threads 50, 60, which intersect at connection points 70 (FIG. 5D). The superimposition of intersecting warp and weft threads 50, 60 produces a conductor loop comprising a plurality of sections 85A, 85B running at right angles to one another, in which strip conductor 85 runs in the form of a helix from the outside to the inside. The two terminal contacts 85C, 85D of strip conductor 85 lead outwards and lie parallel to one another.

Figure 5G:
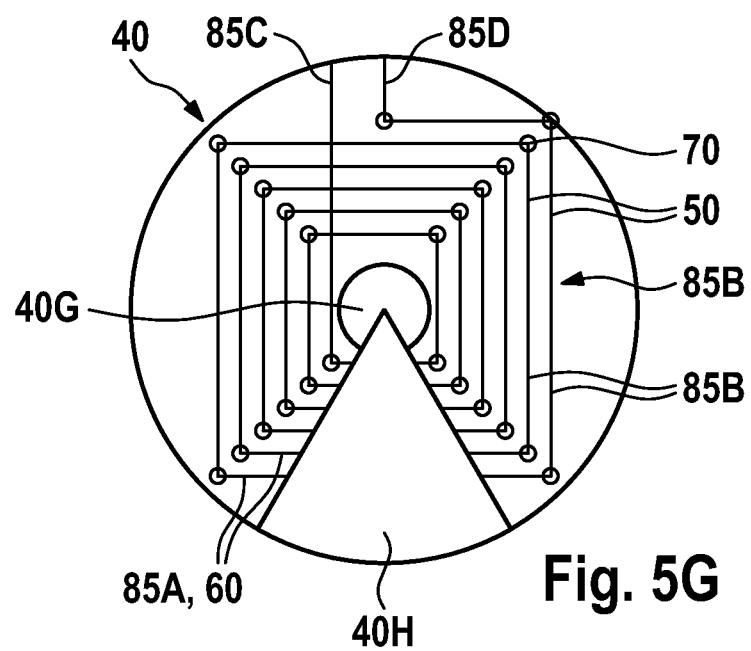
FIG. 5G shows the strip conductor with a woven fabric zone insulated at the upper side.

In order at all events to prevent, in the exemplary embodiments of pad 40 described, the electrically conductive puncture cannula from causing a short circuit between individual sections of the strip conductor, there can be provided at the upper side of the pad an insulating woven fabric zone 40H, in which no conductive threads emerge at the surface. FIG. 5G shows, by way of example, an insulating triangular woven fabric zone 40H at the upper side of circular pad 40. Woven fabric zone 40H extends up to central cutout 40G for the passage of the needle. Any other arbitrary shape is however also possible for the insulation layer. The only crucial factor is that the outward-facing surface of the pad is not electrically conductive at least in the zone beneath the puncture cannula, so that the metallic puncture cannula cannot produce a short circuit. As described above, this can be achieved by the weaving process alone. An additional local insulation layer is then no longer necessary on the finished woven fabric, although it would be possible, but this would increase the outlay and cost.

FIG. 5F again shows all the points of intersection with electrically conductive warp and weft threads 50, 60 over their whole length.

The device for detecting moisture, which comprises only one strip conductor 85 with two terminal contacts (FIGS. 5A-5F), is connected via a two-core connection cable 42 to evaluation unit 41 of monitoring device B (FIG. 2). A terminating resistor is not necessary with this exemplary embodiment. The resistance between terminal contacts 85A, 85B changes depending on the moisture. If the resistance exceeds a preset threshold value, evaluation unit 41 responds.

In the exemplary embodiment with two strip conductors 80, 90 (FIGS. 3 and 4), on the other hand, a terminating resistor R is required, which connects one end of the one strip conductor to the other end of the other strip conductor, so that a conductor loop is formed. Terminating resistor R is incorporated between inner terminal contacts 90C, 90D. Connected to outer terminal contacts 80C, 80D is a two-core connection cable 42, which connects electrically the moisture sensor to evaluation unit 41 of monitoring device B. The total resistance of the conductor loop then consists of the sum of the resistances of the two strip conductors 80, 90 and terminal resistance R. The terminating resistor is a very high-resistance resistor, in particular a resistor of more than 100 kOhms, whereas the strip conductor resistances are low-resistance. The electrically conductive threads can as such have, for example, a length-specific resistance of 100 ohms per meter of thread length. For example, the strip conductor resistances of finished woven strip conductors, including the resistances of all the connection points, are in total less than 1 kOhm.

Evaluation unit 41 of the monitoring device measures the resistance between terminal contacts 80C, 80D. If the pad 40 is wetted with fluid, in particular blood, the resistance measured between the terminal contacts diminishes, so that evaluation unit 41 detects a malfunction.

Evaluation unit 41 also permits a check on the operability of detection device 40. For this purpose, evaluation unit 41 measures the resistance between the terminal contacts. This resistance must correspond to the sum of terminal resistance R and the strip conductor resistance, when pad 40 is not wetted with fluid. If the measured resistance diverges from the terminal resistance by a preset difference, the evaluation unit ascertains that detection unit 40 is not operable, i.e., a strip conductor is interrupted.

Detection device 40 according to the present invention with the two strip conductors has an advantage that the particular routing of the strip conductors permits the displacement of terminating resistor R outside the pad. Straightforward manufacture of the pad is thus made possible. This is because the terminating resistor could not be produced with sufficient reproducibility in the weaving process. The pad can thus be produced solely by weaving without additional process steps. A terminating resistor likewise does not need to be applied on the pad after the weaving process. An advantage of a constantly reproducible terminating resistor thus results, independently of the weaving process.

Figure 6:
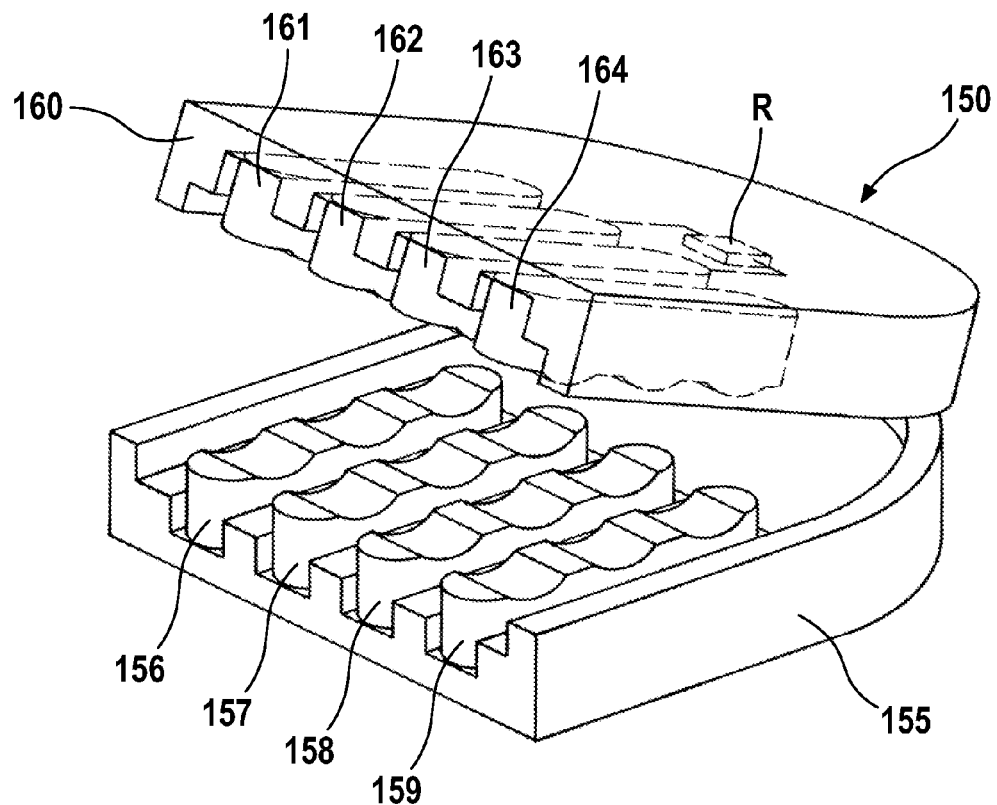
FIG. 6 shows a first exemplary embodiment of the connection part of the device for monitoring a patient access.

FIG. 6 shows a diagrammatic representation of the main elements of a connection part 150 for the connection of pad 40 from FIG. 4 without a cross-shaped cutout to evaluation unit 41 of monitoring device B. In principle, however, pad 40 from FIG. 3 with a cross-shaped cutout can also be connected to connection part 150. Then, however, the cross-shaped cutout cannot be used for fixing the pad.

Connection part 150 is constituted as a clamping device for the clamping of tab 40E of pad 40. It comprises a lower clamp part 155 and an upper clamp part 160, four terminal contacts 156, 157, 158, 159 lying beside one another being disposed in lower clamp part 155 and four terminal contacts 161, 162, 163, 164 lying beside one another being disposed in upper clamp part 160. Upper and lower clamp parts 155, 160 can be clamped together, tab 40E of pad 40 with terminal contacts 80C, 80D, 90C, 90D lying between mutually opposite terminal contacts 156, 157, 158, 159 and 161, 162, 163, 164 of upper and lower clamp parts 155, 160. The two inner terminal contacts 162, 163 of upper clamp part 160 are connected electrically to one another by a terminating resistor R shown only diagrammatically. Terminating resistor R can be an SMD resistor (miniature resistor) integrated into upper clamp part 160.

Figure 7:
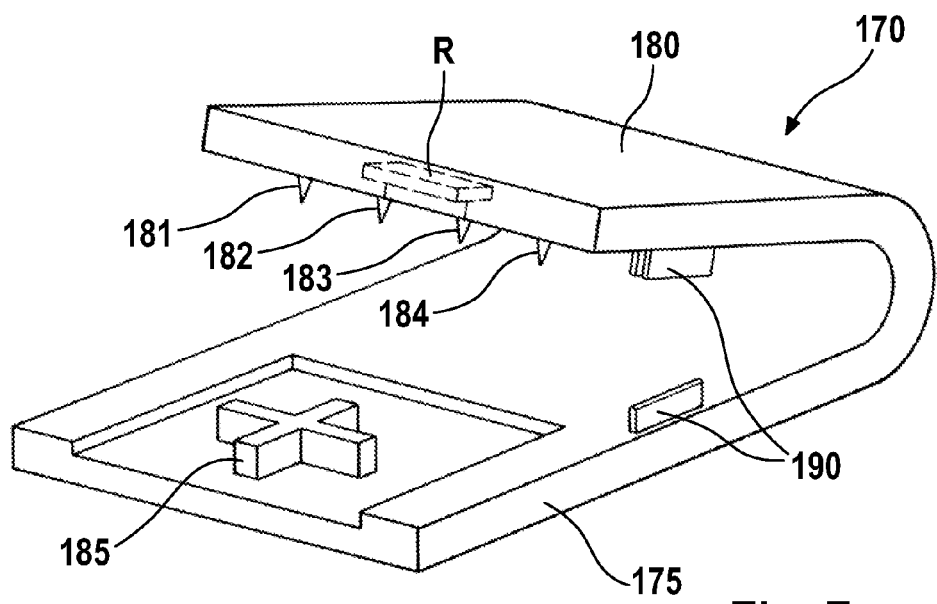
FIG. 7 shows a second exemplary embodiment of the connection part of the monitoring device.

FIG. 7 shows a diagrammatic representation of a second exemplary embodiment of connection part 170 constituted as a clamping device. Connection part 170 comprises legs 175, 180 connected elastically to one another, one leg 175 being longer than other leg 180.

Longer lower leg 175 of connection part 170 represented in FIG. 7 comprises a salient protrusion 185, which corresponds in shape to a cutout of a pad. In the present exemplary embodiment, salient protrusion 185 is cross-shaped, since the matching pad (not shown) comprises a central cross-shaped cutout 40F. Any other arbitrary shape is however also possible.

Shorter upper leg 180 comprises at the underside four terminal contacts 181, 182, 183, 184 lying beside one another, which are constituted as spikes. Latching elements 190, shown only by way of indication, are provided at the opposite inner sides of the two legs 175, 180, so that the legs can be fixed latched tight after being pressed together. In this exemplary embodiment, the two inner terminal contacts 182, 183 of connection part 170 are also connected via a terminating resistor R, which is constituted as an SMD resistor integrated into upper leg 180.

For connection of detection device 40 to monitoring device B, the pad (not shown) is placed between the two legs 175, 180 of connection part 170, so that cross-shaped protrusion 185 engages into cross-shaped cutout 40F of pad 40. The two legs 175, 180 of connection part 180 are then pressed together, terminal contacts 181, 182, 183, 184 of connection part 170 coming into contact with terminal contacts 80C, 80D, 90C, 90D of the pad. The pad is fixed by spike-shaped terminal contacts 181, 182, 183, 184.

Figure 8:
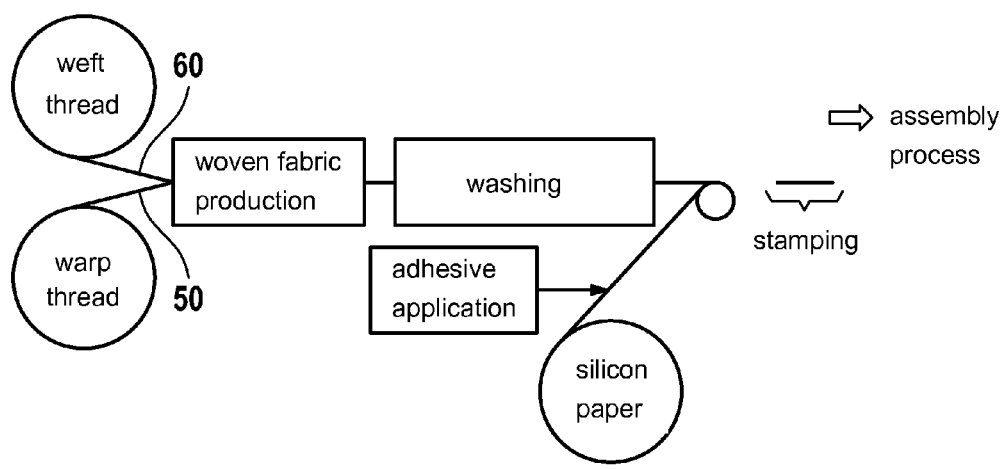
FIG. 8 shows a representation of exemplary process steps for the production of the device for detecting moisture.

FIG. 8 shows the main exemplary process steps of the weaving process for the production of the detection device according to the present invention. Warp threads 50 and weft threads 60 are fed for the production of the preferably multi-layer woven fabric. After the production of the woven fabric, further process steps known to the person skilled in the art take place, which include washing. A covering material with an adhesive layer is then applied to the underside of the continuous length of woven fabric. The adhesive can be applied, for example, using a rotary brush. A silicone paper coated with adhesive is preferably applied to the rear side of the continuous length of woven fabric. Alternatively and particularly preferably, a two-sided self-adherent adhesive film, for example a PET film, is applied to the rear side of the continuous length of woven fabric. The function of an adhesive film lies on the one hand in the provision of a barrier against saturation of the sticking-plaster sensor with the patient's perspiration. On the other hand, a differing adhesive strength can be provided at the upper and lower side by using a two-sided adherent adhesive film. At the side facing towards the patient's skin, the film preferably has a smaller adhesive strength than that at the side facing away from the skin and facing towards the woven fabric. On the side facing towards the skin, the adhesive film preferably has a silicone paper for protection of the adhesive layer.

Instead of silicone paper, use may also be made of a siliconised plastic film. The decisive factor is that the adhesive layer of the sensor can easily be detached from the silicone paper or the siliconised plastic film.

The pads are then separated into single units, for example by stamping or cutting from the continuous length of woven fabric. The cutouts of the pad can also be produced in the stamping or cutting process.

The pads can be packaged individually in a sterile manner or a plurality of pads lying one upon the other can be packaged in a sterile manner. In the case of use of the pad for monitoring a central venous catheter, a sterile pad is preferably used which has been sterilised, for example by the known sterilisation methods ETO (ethylene oxide) or E-beam (electron beam sterilisation). Alternatively, steam sterilisation can also be carried out.

For use, the covering material is pulled off from the pad and the pad is placed with the adhesive layer onto the patient's skin. The puncture with the cannula can then take place. It is however also possible to place the pad on the patient's skin after the puncture if the pad is cut out at the side. The connection part can be connected to the pad before or after the pad is placed on the skin.

FIG. 9 shows a further exemplary embodiment of the device for detecting moisture in a schematic representation, which will again be referred to below as a pad. With the exception of the central cutout, the pad has the same shape as the pad described by reference to FIGS. 3A to 3H. It comprises a central zone 200A with two legs 200B, 200C, which laterally enclose a semicircular cutout 200D. A tab 200E lying opposite the two legs is formed on the central zone.

The electrically conductive warp and weft threads forming an electrically conductive structure are characterised by horizontal and vertical thin lines. In this exemplary embodiment, in contrast with the exemplary embodiments described above, weft threads S run in the vertical direction and warp threads K run in the horizontal direction. The electrically conductive structure is formed by 8 warp threads K[1] to K[8] and 12 weft threads S[1] to S[12], which are disposed at the points of intersection in such a way that they are either connected in an electrically conductive manner or are insulated electrically from one another.

FIG. 10 shows a matrix to illustrate the 88 points of intersection of the 8 warp threads K[1] to K[8] and the 12 weft threads S[1] to S[12]. The points of intersection of two conductive threads which produce a contact are denoted in the matrix by "Cont.", whilst the points of intersection of two conductive threads which form an insulation point are denoted by "Isol." An electrically conductive structure arises, which comprises two strip conductors which each form a conductor loop constituted non-redundant.

In FIG. 9, the electrical contact points at the points of intersection between the electrically conductive warp and weft threads K[i], S[i] are represented as circles. First strip conductor L1A-L1E runs from tab 200E via central zone 200A to left-hand leg 200B and from left-hand leg 200B via the central zone to right-hand leg 200C and from the right-hand leg via the central zone back to the tab of the pad. The start of the respective strip conductor is designated by "A" and the end of the strip conductor is designated by "E". The two ends L1A, L1E of first strip conductor L1A-L1E form the two terminal contacts. Second strip conductor L2A-L2E runs from tab 200E via central zone 200A to left-hand leg 200B and from the left-hand leg via the central zone to right-hand leg 200C and from the right-hand leg via the central zone to the tab of pad 40. The two ends L2A, L2E of second strip conductor L2A-L2E form the second pair of terminal contacts. The terminal contacts are disposed on tab 200E in such a way that terminal contacts L2A and L1E lie between terminal contacts L1A and L2E.

The woven fabric of the exemplary embodiment of FIG. 9 can be a three-layer woven fabric extending over the whole sensor, said three-layer woven fabric comprising a first non-conductive layer, a second conductive layer with conductive threads in a first direction and a third conductive layer with conductive threads in a second direction, wherein the second direction is essentially at right angles to the first direction.

An alternative exemplary embodiment provides for a woven fabric, wherein the number of layers differs locally. Thus, the woven fabric can comprise a different number of layers in individual zones of the sensor. Three different zones can be constituted, wherein the first zone forms a contact point at which conductive threads intersect in a contacting manner, the second zone forms an insulation point at which an insulating thread is located between conductive threads, and the third zone forms neither a contact point nor an insulation point.

A particularly preferred exemplary embodiment makes provision such that local zones forming a contact point and local zones forming neither a contact point nor an insulation point comprise a total of two layers. Located in the first layer are the conductive threads running in the first direction as well as in the second direction. The second (uppermost) layer forms a non-conductive cover layer, which ensures that the sensor is advantageously not sensitive to being touched. If the sensor were sensitive to touch, touching of the exposed sensor area of the sensor stuck on the patient, for example with the fingers, would lead to a false alarm. Such touching of the sensor can for example be caused by the patient himself or by the medical staff. The threads of this insulating second layer dip partially into the first layer, as a result of which a mechanical bond between the first and second layer is produced.

The particularly preferred exemplary embodiment also provides for a local zone forming an insulation point, which comprises a total of four layers. Located in the first (lowest) layer are conductive threads running in the first direction. The second layer comprises a layer of non-conductive threads, which insulates the first layer from the third layer. Conducting threads running in the second direction are located in the third layer. The fourth (uppermost) layer is formed by a non-conductive cover layer, which advantageously makes the sensor insensitive to touch.

The insulation point described above can for example be provided at the points designated by "Isol." in FIG. 10. 68 insulation points emerge in this exemplary embodiment. The insulation with respect to the skin is achieved in this exemplary embodiment with an insulating adhesive film.

The pad with the locally different zones has a differing thickness. A particular advantage of this exemplary embodiment is to be found in the material saving, because the pad has to have a sufficient thickness only at the points where electrically conductive threads have to be insulated from one another. The material saving permits particularly cost-effective production of the sensor.

The pad of FIG. 9 can be connected to a connection part, which differs from the connection part described by reference to FIG. 6 solely in that terminating resistor R is connected to an inner and an outer terminal contact.

Figure 11:
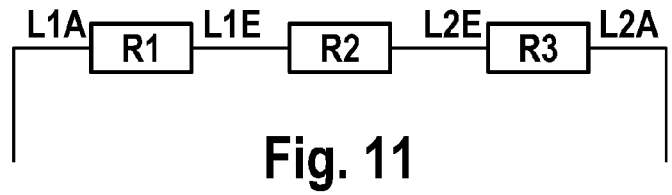
FIG. 11 shows an electrical equivalent circuit diagram of the device of FIG. 9.

FIG. 11 shows the electrical equivalent circuit diagram of the electrically conductive structure of the pad connected to the connection part. The equivalent circuit diagram is a series circuit of resistor R1 of first strip conductor L1A-L1E, resistor R2 of the terminating resistor and resistor R3 of second strip conductor L2A-L2E. Resistors R1 and R3 of the first and second strip conductors should each preferably not be greater than 200Ω.

Figure 12:
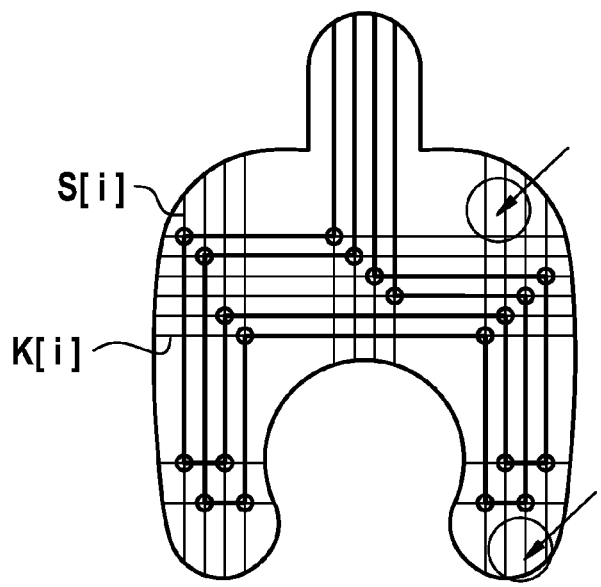
FIG. 12 shows a representation to illustrate sensitive regions of the device of FIG. 9.

The sensitivity of the pad to moisture is produced not solely directly in the zone of the conductive structure of warp and weft threads, but also in the edge zones of the pad, since the warp and weft threads extend up to the edge of the pad. In FIG. 12, by way of example, two edge zones of the pad are marked with circles, in which the pad is sensitive to moisture. Moreover, the sensitivity of the pad to moisture can be adjusted with a non-conductive woven-fabric cover layer.

Figure 13:
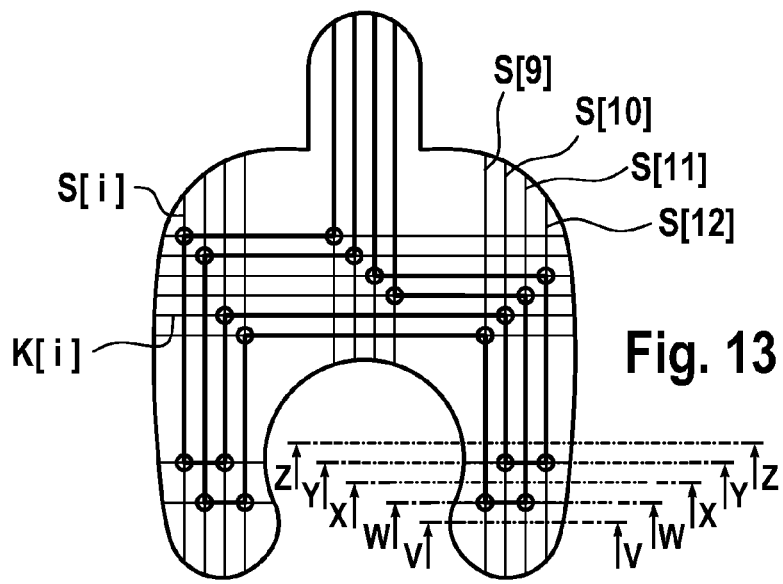
FIG. 13 shows a representation to illustrate different sections through the device of FIG. 9.
Figure 14A:
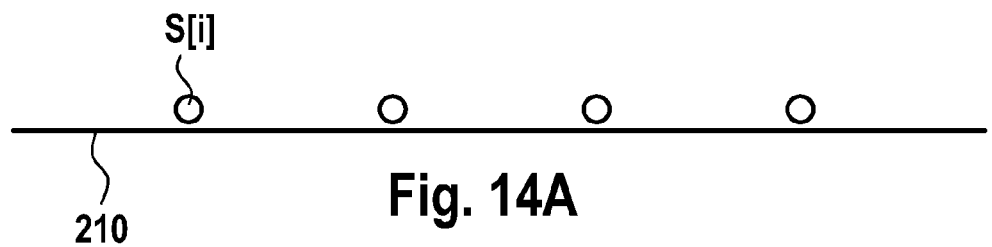
FIG. 14A to FIG. 14E show a representation to illustrate the linkages between warp and weft threads of the device of FIG. 9 in the sectional planes of FIG. 13.
Figure 14B:
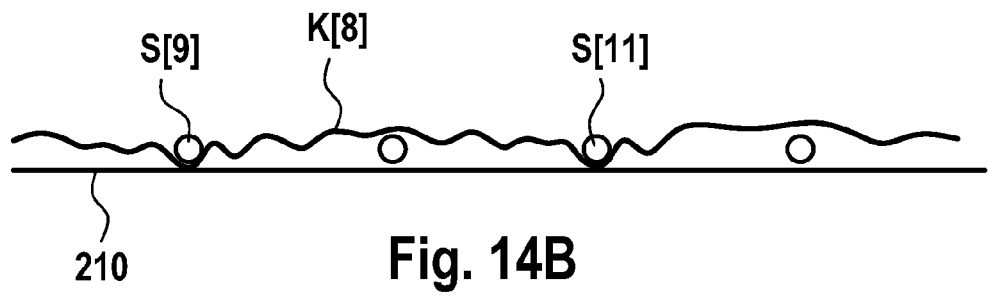
Figure 14C:
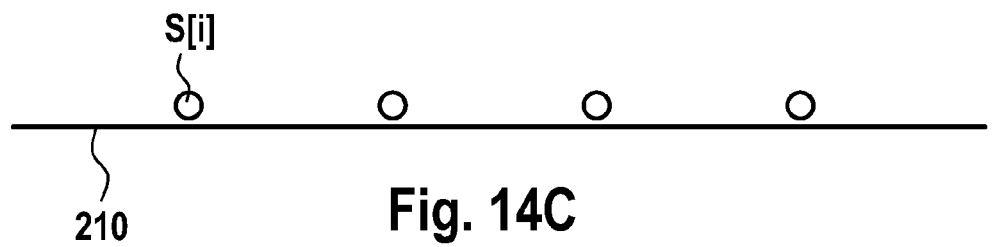
Figure 14D:
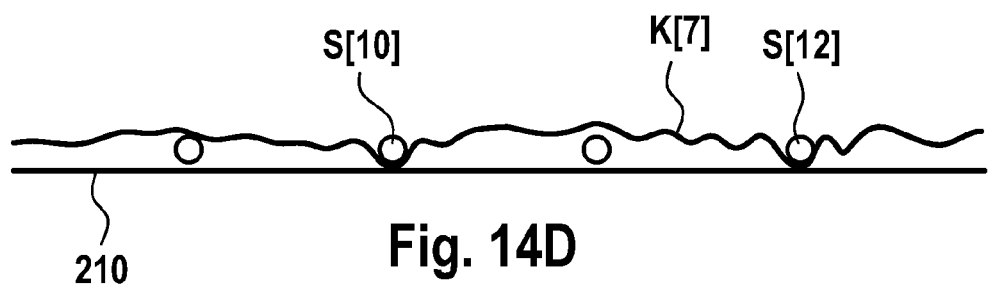
Figure 14E:
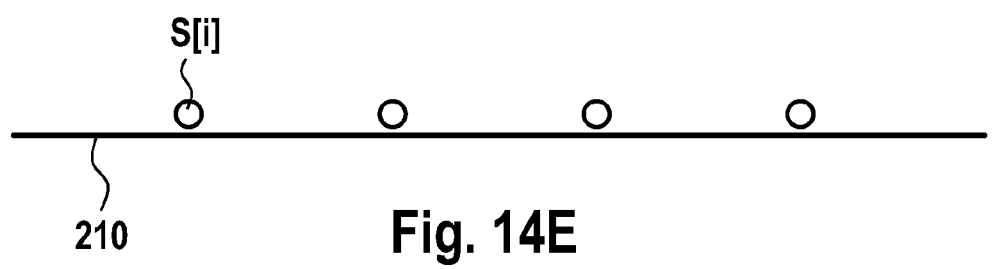

FIGS. 14A to 14E show sections through the cover 210 (liner), for example a silicone paper, and the linkages of the warp and weft threads of the pad in the sectional planes, which are represented in FIG. 13. The warp threads K[i] and weft threads S[i] are not linked in sectional plane V-V, since warp threads are not present in this plane. Warp thread K[8] is linked to weft thread S[9] and warp thread K[8] is linked to weft thread S[11] in sectional plane W-W, so that an electrical connection is produced between warp and weft thread. Warp threads K[i] and weft threads S[i] are not linked in sectional plane X-X, since warp threads are not present in this plane. Warp thread K[7] is linked to weft thread S[10] and warp thread K[7] is linked to weft thread S[12] in sectional plane Y-Y, so that an electrical connection is produced between warp and web thread. Warp threads K[i] and weft threads S[i] are not linked in sectional plane Z-Z, since warp threads are not present in this plane.

Figure 15:
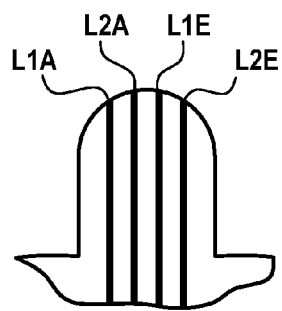
FIG. 15 shows an exemplary embodiment of the tab of the device for detecting moisture.

FIG. 15 shows in a schematic representation the arrangement of terminal contracts L1A, L1E and L2A, L2E on tab 200E of the exemplary embodiments of the pad described above. In these exemplary embodiments, the ends of the warp or weft threads run with an identical spacing up to the edge of the tab. The threads are located at the surface of tab 200E in order to form terminal contacts L1A, L1E and L2A, L2E. In order to avoid a short circuit between the terminal contacts of the connection part, the width or the diameter of the terminal contacts of the connection part must be smaller than the distance between terminal contacts L1A and L2A, L2A and L1E as well as L1E and L2E of the pad. The width or diameter of the terminal contacts of the connection part is therefore limited.

Figure 16:
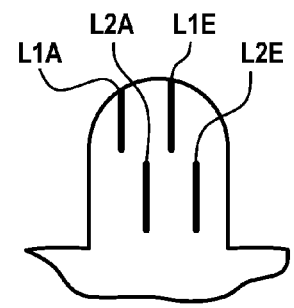
FIG. 16 shows a further exemplary embodiment of the tab of the device for detecting moisture.

FIG. 16 shows an alternative exemplary embodiment of the arrangement of the terminal contacts on tab 200E of the pad in a schematic representation, wherein the terminal contacts L1A and L1E of the one strip conductor L1A-L1E are disposed offset with respect to terminal contacts L2A and L2E of the other strip conductor L2A-L2E. Terminal contacts L1A and L1E of the one strip conductor are located on the upper half and terminal contacts L2A and L2E of the other strip conductor are located on the lower half of tab 200E. Since the pad comprises an insulating woven-fabric cover layer at the surface, a targeted "dipping" of the threads is possible. In the exemplary embodiment of FIG. 16, weft threads S[5] and S[7] (FIG. 9) lie in the lower half of the tab beneath the cover layer and weft threads S[6] and S[8] (FIG. 9) lie in the upper half of the tab beneath the cover layer, so that the terminal contacts of the connection part can have a greater width or a greater diameter than in the case of the exemplary embodiment of FIG. 15, without a short circuit occurring between contacts L1A and L1E and respectively L2A and L2E.

Figure 17A:
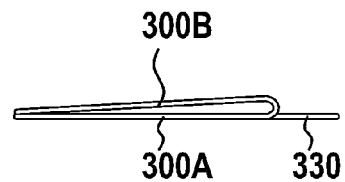
FIG. 17A shows a further exemplary embodiment of the device for detecting moisture in a side view.

Further alternative exemplary embodiments of the pad are described below, which differ from one another in the shape and the course of the strip conductors. FIG. 17A shows in a side view a pad 300 divided into two halves, wherein the one half is folded over onto the other half after application on the patient's skin. FIG. 17A shows the side view of the pad after the folding-over.

Figure 17B:
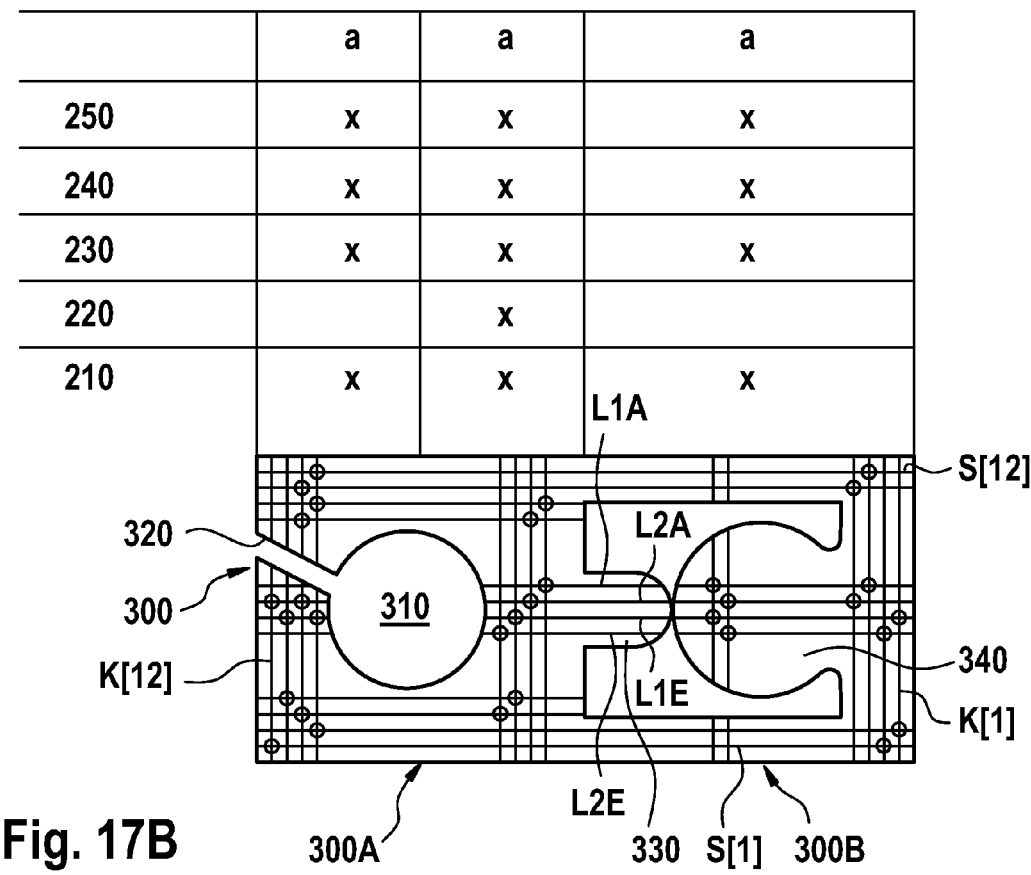
FIG. 17B shows the device for detecting moisture of FIG. 17A in plan view together with a representation of the individual layers in a table.

FIG. 17B represents the pad of FIG. 17A before the folding-over in plan view. The first half of the pad, which lies on the patient's skin, is designated by 300A, whilst the second half of the pad to be folded over is designated by 300B. The pad comprises a plurality of layers, which are described in FIG. 17B in the form of a table assigned to the pad, which has lines and columns assigned to the individual zones of the pad. First half 300A of pad 300 is divided into two fields (two columns in the table) of equal size. One field (one column of the table) is assigned to second half 300B of pad 300. The lines in the table denote the individual layers.

The lowest layer forms a cover 210, for example a peel-off film, with which an adhesion layer 220 adhering to the patient's skin is covered. As can be seen from the table, cover 210 is located at the underside of the two halves 300A and 300B of pad 300, since all the fields are marked with "X". Adhesion layer 220, on the other hand, is located in the central zone of first half 300A of pad 300.

Adhesion layer 220 is followed by a layer 230 impermeable to moisture and liquid, for example a PET film, which extends over the whole area of the pad. Located on the upper side of the PET film is an adhesive coating 240, on which a multi-layer woven fabric 250 with an electrically conductive structure lies, said structure being formed by 12 warp threads K[1] to K[12] and 12 weft threads S[1] to S[12].

The points of intersection at which an electrical connection between the warp and weft threads is produced are again marked with circles in FIG. 17B. The intersecting warp and weft threads are again disposed in such a way that they form a first and a second strip conductor, the ends whereof form terminal contacts L1A, L1E and L2A, L2E of pad 300. The strip conductors are disposed in such a way that the two electric circuits are not redundant.

First half 300A of rectangular pad 300 comprises a central circular cutout 310, from which an obliquely running narrow cutout 320 extends up to the narrow side of the first half of the pad. Second half 300B of pad 300 is cut out in such a way that a tab 330 for terminal contacts L1A, L1E and L2A, L2E arises on the inner side and a circular cover 340 for circular cutout 310 of the first half of the pad arises on the outer side. Circular cover 340 of the second half is larger than circular cutout 310 of the first half, so that the circular cutout of the first half is completely covered by the circular cover when the second half of the pad is folded onto the first half.

Pad 300 is used as follows. After the cannula (not represented) has been put in place and peel-off film 210 has been pulled off, the pad is stuck onto the patient's skin with adhesion layer 220. Since an incision is made into the pad at the side, the pad can be moved laterally over the cannula already in place, so that the cannula lies in circular cutout 310 of the first half of the pad. Second half 300B of the pad is now folded onto first half 300A (FIG. 17A). Since only the central zone of the first half of the pad adheres to the patient's skin, the second half of the pad can easily be gripped for this purpose. Second half 300B can be fixed on the skin at the puncture point, for example with an adhesive tape. After the folding of the pad, tab 330 lies exposed with terminal contacts L1A, L1E and L2A, L2E, so that the connection part can be connected.

Regarding the pad, the electrically conductive structure with the warp and weft threads is located at the upper side of the pad, so that the pad is sensitive at the upper side. This becomes clear in the table from the designation "a", which stands for sensitivity at the upper side. After the folding-over of second half 300B onto first half 300A of pad 300, the pad also becomes sensitive at the underside in the region of circular cutout 310, which is located in the immediate vicinity of the puncture point, since this zone is covered by cover 340 sensitive at the upper side before the folding.

Figure 18:
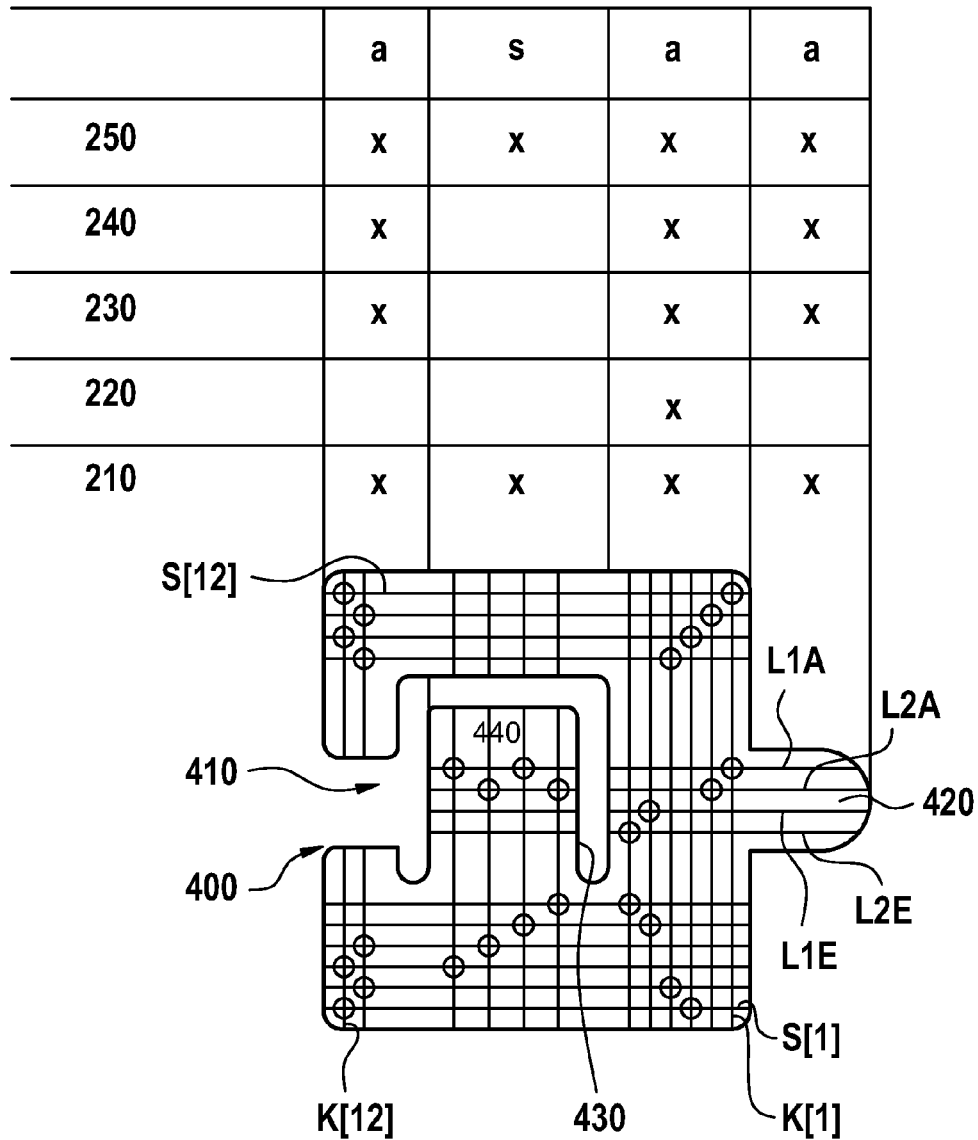
FIG. 18 shows a further exemplary embodiment of the device for detecting moisture together with a representation of the individual layers in a table.

FIG. 18 shows a further exemplary embodiment of pad 400, which however is not folded over, in contrast with pad 300 from FIGS. 17A and 17B. The parts corresponding to one another are provided with the same reference numbers. The structure of the multi-layered pad emerges from the table and the representation of the points of intersection, at which an electrical connection between warp and weft threads is produced. The intersecting warp and weft threads are again disposed in such a way that they form a first and a second strip conductor, the ends whereof are the terminal contacts of the pad. The electrically conductive structure is formed by 12 warp threads K[1] to K[12] and 12 weft threads S[1] to S[12].

Pad 400 is essentially rectangular in the exemplary embodiment of FIG. 18. At one side, the pad comprises a, for example, rectangular cutout 410, whilst the pad comprises a tab 420 at the side lying opposite the cutout. Rectangular cutout 410 at one side of the pad continues into a narrow gap 430 which severs the strip conductors, so that the two electric circuits of the electrically conductive structure are not redundant. The width of gap 430 is dimensioned such that abutting surfaces of conductive threads cannot cause a short circuit. In the exemplary embodiment, gap 430 has for example a U-shaped course, the gap partially surrounding a central zone 440 of the pad which lies on the puncture point.

It can be seen from the table that pad 400 is sensitive at the underside in central zone 440 which is surrounded by narrow gap 430, since this zone is designated by "s" in the table, which stands for sensitivity at the underside. In the remaining zones, on the other hand, the pad is sensitive at the upper side ("a"). The sensitivity at the underside of the pad is achieved by the fact that PET film 230 impermeable to water and moisture is not present in central zone 440, which emerges from the table. Adhesion layer 220 and adhesive coating 240 are also absent in this zone (table).

An advantage of this exemplary embodiment lies in the fact that the puncture point is additionally covered by a woven fabric sensitive at the underside, so that the pad is sensitive on both sides. Leakages of blood at the puncture point can be immediately and reliably detected by the pad which is also sensitive at the underside. Since the remaining zones are sensitive at the upper side, the cannula lying beneath the pad cannot cause a short circuit.

Figure 19:
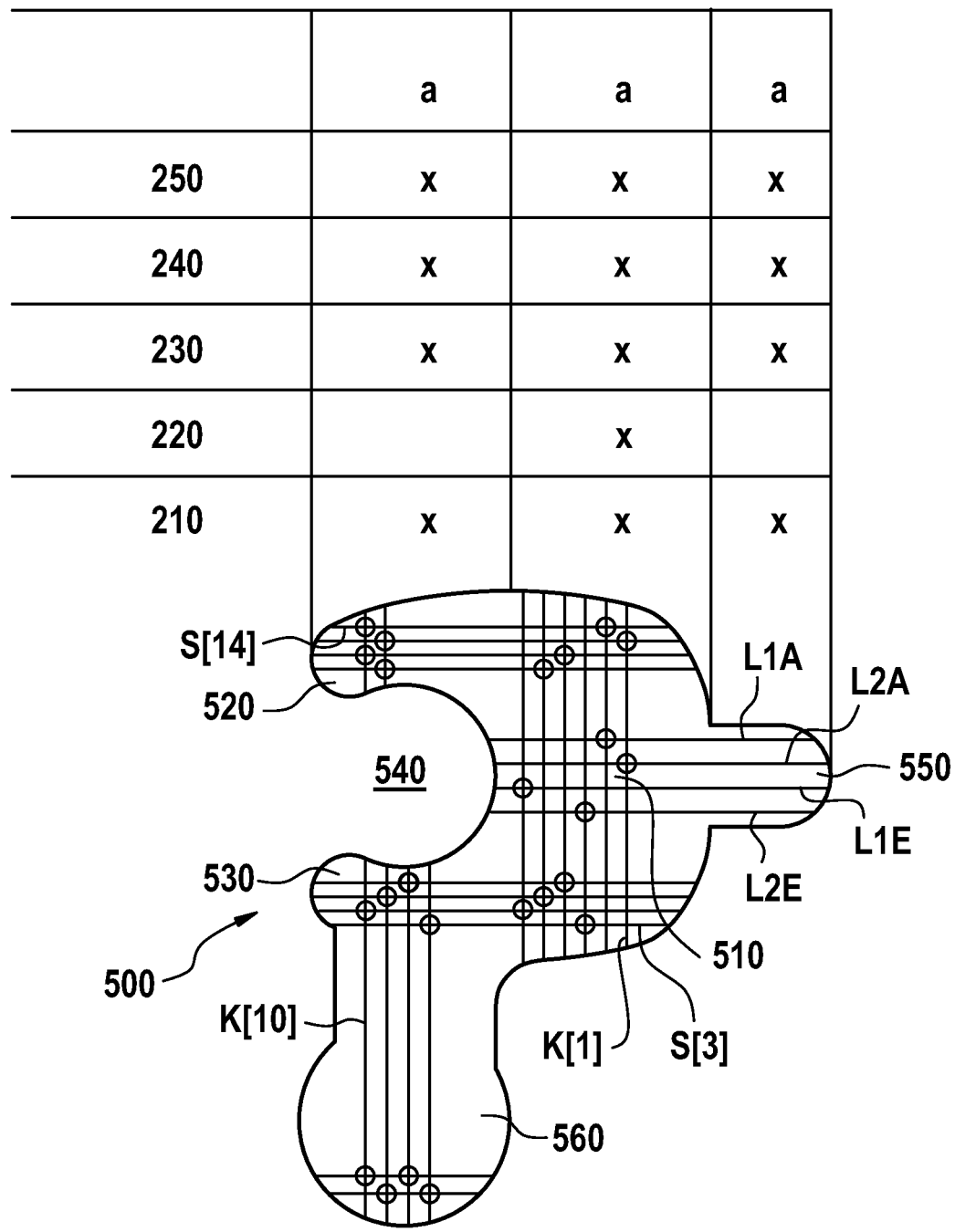
FIG. 19 shows a further exemplary embodiment of the device for detecting moisture together with a representation of the individual layers in a table.

A further exemplary embodiment of pad 500 which is sensitive on both sides, but which is folded over, is shown in FIG. 19. The parts corresponding to one another are again provided with the same reference numbers. The intersecting warp and weft threads are again disposed in such a way that they form a first and a second strip conductor, the ends whereof form the terminal contacts of the pad, wherein the two electric circuits are not redundant. The electrically conductive structure is formed by 10 warp threads K[1] to K[10] and 14 weft threads S[1] to S[14].

The pad comprises a central section 510 with two legs 520, 530, which laterally surround a semicircular cutout 540. Formed on central section 510 is a tab 550 with terminal contacts L1A, L1E and L2A, L2E, said tab lying opposite the two legs 520, 530. Pad 500 further comprises a lateral cover 560 for semicircular cutout 540, which is formed on one of the two legs 520, 530. Lateral cover 560 is dimensioned such that semicircular cutout 540 of the pad, in which the cannula lies, is completely covered after the folding-over of the cover.

As emerges from the table, pad 500 is sensitive only on the upper side before the folding-over of cover 560. After the folding-over of the cover, the pad is also sensitive at the underside in the region of semicircular cutout 540, so that leakages of blood occurring at the puncture point can be reliably detected.

Figure 20:
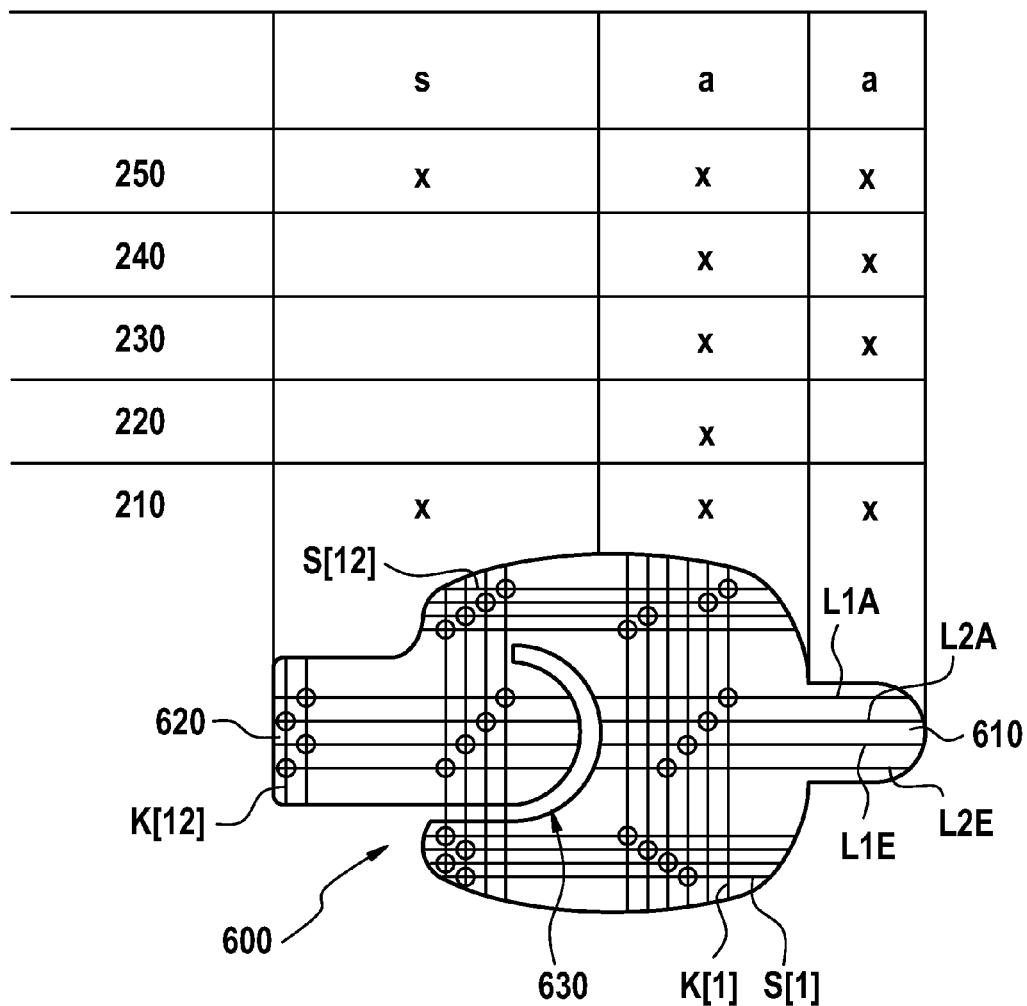
FIG. 20 shows a further exemplary embodiment of the device for detecting moisture together with a representation of the individual layers in a table.

FIG. 20 shows a further exemplary embodiment of pad 600, which does not need to be folded over in order to be sensitive on both sides. The electrically conductive structure of the pad is formed by 12 warp threads K[1] to K[12] and 12 weft threads S[1] to S[12]. At the side lying opposite tab 610, pad 600 comprises an extension 620, which lies in the region of the puncture point. In the region of extension 620, the pad is sensitive at the underside, in the remaining zones at the upper side (table). A semicircular narrow incision 630 following on from the extension again severs the threads in such a way that the two electric circuits of the electrically conductive structure are not redundant.

Figure 21:
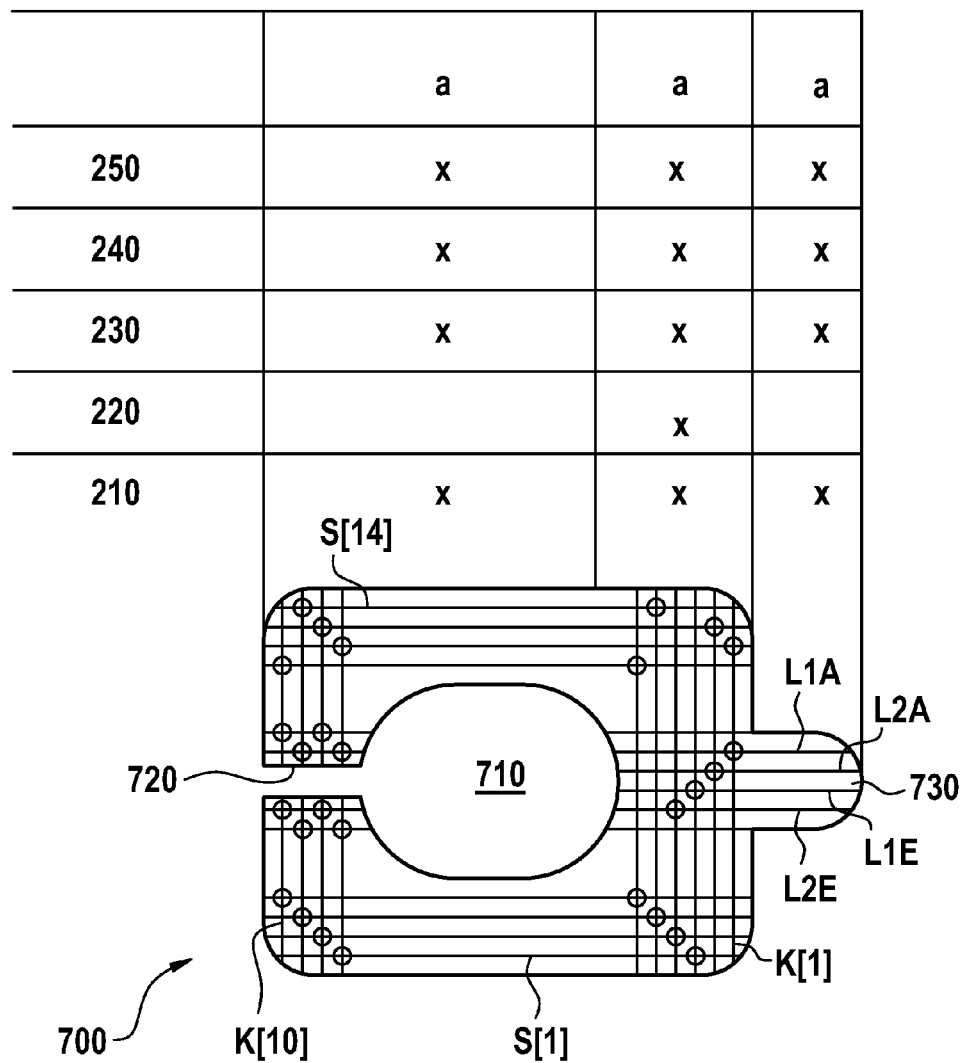
FIG. 21 shows a further exemplary embodiment of the device for detecting moisture together with a representation of the individual layers.

FIG. 21 shows a further exemplary embodiment of a pad 700, which is sensitive only at the upper side (table). The electrically conductive structure of the pad is formed by 10 warp threads K[1] to K[10] and 14 weft threads S[1] to S[14]. The pad is characterised by a central, for example oval, cutout 710, from which a narrow incision 720 extends up to the side of the pad lying opposite tab 730 with contact terminals L1A, L1E and L2A, L2E. The cannula lies in central cutout 710. Since the cannula is almost completely surrounded by the pad, leakages of blood can be reliably detected also in the opposite direction to the needle.

Figure 22:
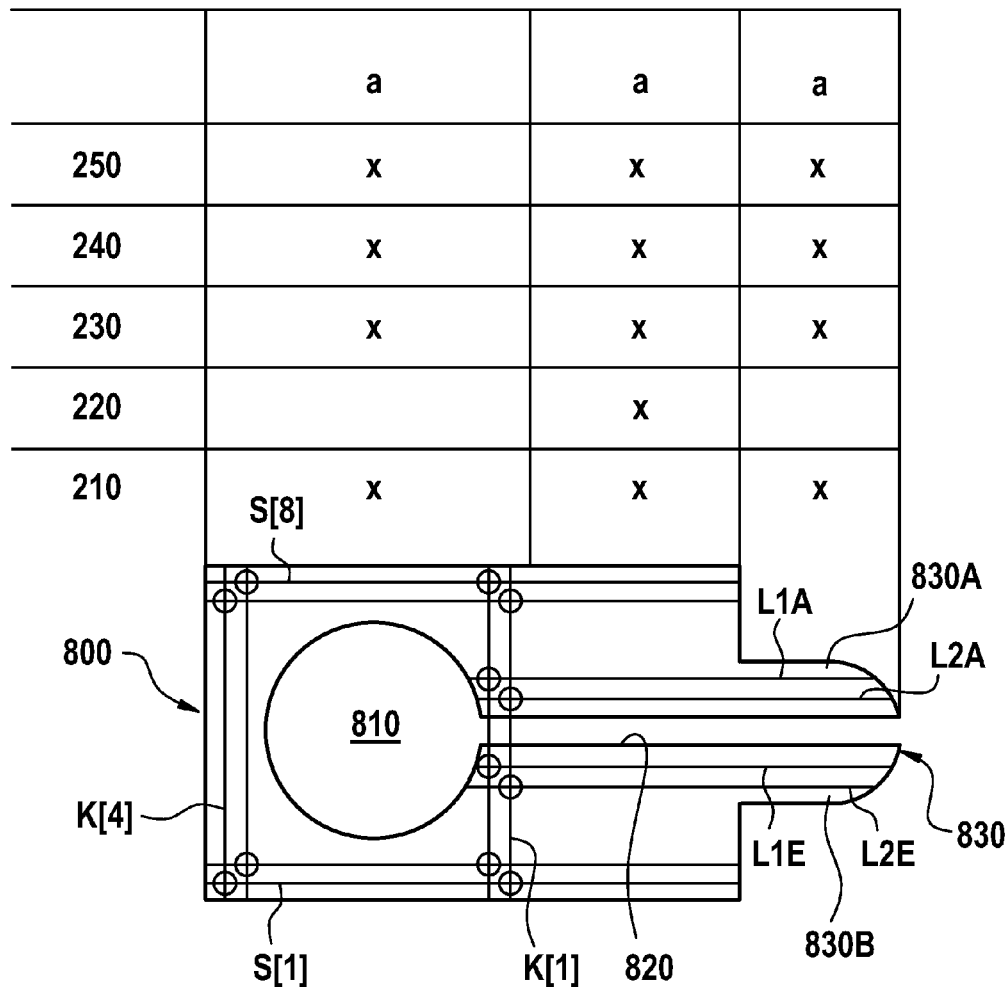
FIG. 22 shows a further exemplary embodiment of the device for detecting moisture together with a representation of the individual layers.

A further exemplary embodiment of a pad 800 sensitive only at the upper side is shown in FIG. 22. The electrically conductive structure of the pad is formed by 4 warp threads K[1] to K[4] and 8 weft threads S[1] to S[8]. The pad differs from the pad of FIG. 21 essentially in that insertion 820 proceeding from central cutout 810 extends not to the side lying opposite tab 830, but through the tab itself. Tab 830 is thus divided into two halves 830A, 830B, on which two terminal contacts L1A, L1E and respectively L2A, L2E are disposed in each case. Central cutout 810 is not oval, but circular in this exemplary embodiment.

Figure 23:
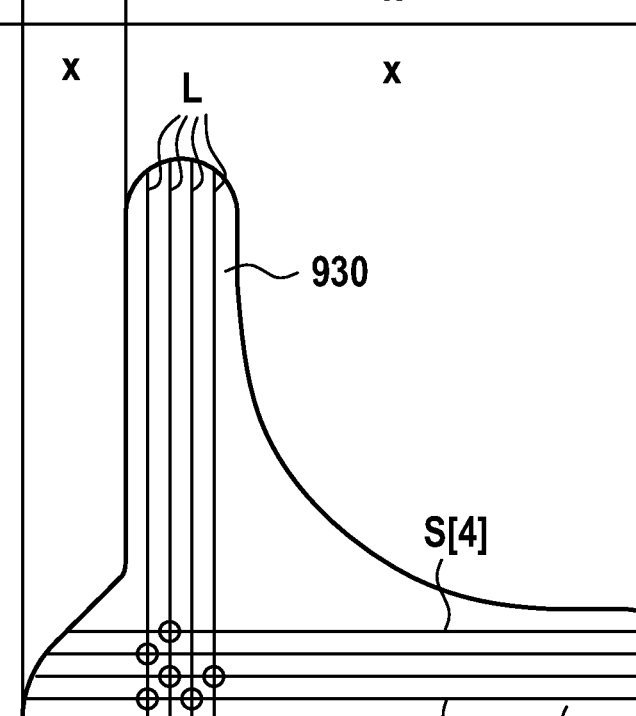
FIG. 23 shows a further exemplary embodiment of the device for detecting moisture together with a representation of the individual layers.

A further exemplary embodiment is shown in FIG. 23, which is sensitive on both sides. Pad 900 comprises a central section 910, which is sensitive at the underside. The pad is placed on the puncture point with central section 910. The electrically conductive structure of the pad is formed by 4 warp threads K[1] to K[4] and 4 weft threads S[1] to S[4], which intersect in a central section 910. The points of intersection at which the threads come into contact are marked by circles.

This exemplary embodiment differs from the other pads in particular by the fact that the pad comprises two tabs 920, 930 with in each case four terminal contacts L1A, L1E and respectively L2A, L2E, which are formed on central section 910. The two tabs 920, 930 can for example enclose an angle of 90°. An advantage of this exemplary embodiment lies in the fact that the connection part can be connected to the pad at two different points. The conductor loop is constituted non-redundant in this exemplary embodiment.

The invention claimed is:
1. A device for detecting moisture for use with a device for monitoring an access to a patient for an apparatus with which at least one of a fluid is fed to the patient or is carried away from the patient via a hose line, the device for detecting moisture comprising:
a textile two-dimensionally extending fabric configured to be placed onto a patient's skin, said textile two-dimensionally extending fabric comprising non-conductive warp threads, non-conductive weft threads, conductive warp threads and conductive weft threads interwoven at least partially in a same layer of the fabric disposed such that an electrically conductive structure as a moisture sensor is formed,
wherein the electrically conductive structure comprises at least one of:
a first strip conductor and a second strip conductor, ends of the first and second strip conductors being formed as terminal contacts, and the first strip conductor and the second strip conductor being disposed lying beside one another in a plurality of sections;
a strip conductor formed as a closed conductor loop, ends of the strip conductor being formed as terminal contacts, and the strip conductor comprising a plurality of sections disposed lying beside one another; or a plurality of electrically conductive sections running in a first direction and a plurality of electrically conductive sections running in a second direction, the first and second directions being at right angles to one another.

2. The device according to claim 1, wherein the textile two-dimensionally extending fabric is formed at least partially as a woven fabric with a plurality of layers.

3. The device according to claim 2, wherein the electrically conductive and electrically non-conductive warp and weft threads are disposed in the multi-layer woven fabric such that:
a layer configured to be placed on the patient's skin, which is non-conductive, a layer in which electrically conductive sections of a strip conductor run in a first direction, and a layer in which electrically conductive sections of the strip conductor run in a second direction, are formed.

4. The device according to claim 3, wherein the electrically conductive and electrically non-conductive warp and weft threads are disposed in the multi-layer woven fabric such that an intermediate layer, which is not electrically conductive, is situated between the layer in which the sections of the strip conductor run in the first direction and the layer in which the sections of the strip conductor run in the second direction.

5. The device according to claim 3, wherein, in order to create electrical contact points, electrically conductive warp threads partially change position in the multi-layer woven fabric, such that electrically conductive warp and weft threads come into contact at points of intersection.

6. The device according to claim 1, wherein the sections of the strip conductors are formed by one of a plurality of electrically conductive warp threads and a plurality of electrically conductive weft threads running beside one another.

7. The device according to claim 6, wherein the textile two-dimensionally extending fabric is cut out such that a part of the one of the plurality of electrically conductive warp threads and the plurality of electrically conductive weft threads running beside one another is severed.

8. The device according to claim 7, wherein the textile two-dimensionally extending fabric comprises a circular cutout or a cross-shaped cutout.

9. The device according to claim 1, wherein the textile two-dimensionally extending fabric is U-shaped.

10. The device according to claim 1, wherein the textile two-dimensionally extending fabric is circular.

11. The device according to claim 1, wherein the textile two-dimensionally extending fabric comprises a tab on which the terminal contacts are disposed.

12. The device according to claim 1, wherein the textile two-dimensionally extending fabric comprises a section with a cutout and a section with a cover for the cutout, wherein the electrically conductive structure is formed such that the textile two-dimensionally extending fabric is sensitive to moisture at an upper layer.

13. The device according to claim 1, wherein:
the access is a vascular access in an extracorporeal blood treatment;
the fluid is a patient's blood;
the hose line includes an arterial hose line and a venous hose line;
the device for monitoring an access is configured to monitor the vascular access; and
the patient's blood is carried away from the patient via the arterial hose line which has an arterial cannula and is fed to the patient via the venous hose line which has a venous puncture cannula.

14. A device for monitoring an access to a patient for an apparatus with which at least one of a fluid is fed to the patient or a fluid is carried away from the patient via a hose line, the device for monitoring comprising:
a device for detecting moisture according to claim 1.

15. The device according to claim 14, further comprising:
an evaluation unit which is connected to the device for detecting moisture.

16. The device according to claim 15, further comprising:
a connection part to which the device for detecting moisture is connected.

17. The device according to claim 16, wherein the connection part comprises four terminal contacts, two of the four terminal contacts being connected to a connection cable in order to produce an electrical connection between the evaluation unit and the device for detecting moisture, and a remaining two of the four terminal contacts being connected electrically to one another via a terminating resistor.

18. The device according to claim 17, wherein the connection part is formed as a clamping device for clamping the textile two-dimensionally extending fabric.

19. A blood treatment apparatus with an extracorporeal blood circuit, comprising:
an arterial blood line with an arterial cannula and a venous blood line with a venous cannula, and a device for monitoring the vascular access according to claim 14.

20. The device according to claim 14, wherein:
the access is a vascular access in an extracorporeal blood treatment;
the fluid is a patient's blood;
the hose line includes an arterial hose line and a venous hose line;
the device for monitoring an access is configured to monitor the vascular access; and
the patient's blood is carried away from the patient via the arterial hose line which has an arterial cannula and is fed to the patient via the venous hose line which has a venous puncture cannula.

21. A method for production of devices for detecting moisture for use with a device for monitoring an access to a patient for an apparatus with which at least one of a fluid is fed to the patient and a fluid is carried away from the patient via a hose line, the method comprising:
weaving a textile two-dimensionally extending fabric comprising non-conductive warp threads, non-conductive weft threads, conductive warp threads and conductive weft threads, the conductive and non-conductive warp and weft threads interwoven at least partially in a same layer of the fabric being disposed such that the conductive and non-conductive warp and weft threads form an electrically conductive structure; and
separating individual devices configured to detect moisture into single units.

22. The method according to claim 21, further comprising:
applying an adhesive layer on a side of the textile two-dimensionally extending fabric to be placed on a patient's skin, and applying a covering material covering the adhesive layer.

23. The method according to claim 22, wherein the adhesive layer is impermeable to moisture.

24. The method according to claim 21, wherein:
the access is a vascular access in an extracorporeal blood treatment;
the fluid is a patient's blood;
the hose line includes an arterial hose line and a venous hose line;

the device for monitoring an access is configured to monitor the vascular access; and the patient's blood is carried away from the patient via the arterial hose line which has an arterial cannula and is fed to the patient via the venous hose line which has a venous puncture cannula.

* * * * *